(12) United States Patent
Ferrari et al.

(10) Patent No.: US 11,668,721 B2
(45) Date of Patent: Jun. 6, 2023

(54) METHODS FOR DIAGNOSING AND TREATING BICUSPID AORTIC VALVE AND/OR AORTOPATHIES

(71) Applicant: THE TRUSTEES OF THE UNIVERSITY OF PENNSYLVANIA, Philadelphia, PA (US)

(72) Inventors: Giovanni Ferrari, Philadelphia, PA (US); Emanuela Branchetti, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1227 days.

(21) Appl. No.: 14/895,335

(22) PCT Filed: Jun. 3, 2014

(86) PCT No.: PCT/US2014/040662
§ 371 (c)(1),
(2) Date: Dec. 2, 2015

(87) PCT Pub. No.: WO2014/197460
PCT Pub. Date: Dec. 11, 2014

(65) Prior Publication Data
US 2016/0109458 A1    Apr. 21, 2016

Related U.S. Application Data

(60) Provisional application No. 61/831,067, filed on Jun. 4, 2013.

(51) Int. Cl.
| | |
|---|---|
| *A61B 6/03* | (2006.01) |
| *G01N 33/68* | (2006.01) |
| *A61B 8/08* | (2006.01) |
| *A61B 8/12* | (2006.01) |
| *A61B 90/00* | (2016.01) |

(52) U.S. Cl.
CPC .......... *G01N 33/6854* (2013.01); *A61B 6/03* (2013.01); *A61B 8/0883* (2013.01); *A61B 8/12* (2013.01); *G01N 33/6893* (2013.01); *A61B 2090/374* (2016.02); *G01N 2333/70503* (2013.01); *G01N 2800/324* (2013.01); *G01N 2800/329* (2013.01); *G01N 2800/52* (2013.01)

(58) Field of Classification Search
None
See application file for complete search history.

(56) References Cited

U.S. PATENT DOCUMENTS

2007/0224643 A1   9/2007   McPherson et al.
2012/0282637 A1   11/2012  Huber et al.

FOREIGN PATENT DOCUMENTS

WO    WO 2010-005531 A2   1/2010
WO    WO-2011042548 A1 *  4/2011  ............. C07K 16/28

OTHER PUBLICATIONS

Cook et al (Int J Cardiol 133: 95-101, 2009).*
Gil-Marom et al. (34th Int Conf IEEE EMBS, 637-640, 2012).*
Park etal (Front Biosc 16: 486-497, 2011—abstract only).*
Mitchell et al. (Circulation 121: 505-511, 2010).*
Ayad et al., "Accuracy of Two-Dimensional Echocardiography in Determining Aortic Valve Structure in Patients >50 Years of Age Having Aortic Valve Replacement for Aortic Stenosis", The American Journal of Cardiology, Dec. 2011, 108(11), 1589-1599.
Barlovic et al., "Cardiovacular Disease: What's All the AGE/RAGE About?", Cardiovascular & Haematological Disorders, Mar. 2010, 10(1), 7-15.
Barlovic et al., "RAGE biology, atherosclerosis and diabetes", Clinical Science, Apr. 2011, 121(2), 43-55.
Basta, G., "Receptor for advanced glycation endproducts and atherosclerosis: From basic mechanisms to clinical implications", Atherosclerosis, 2008, 196, 9-21.
Basta et al., "Circulating soluble receptor for advanced glycation end-product levels are decreased in patiens with calcific aortic valve stenosis", Atherosclerosis, 2010, 210, 614-618.
Cotrufo et al., "Different patterns of extracellular matrix protein expression in the convexity and the concavity of the dilated aorta with bicuspid aortic valve: preliminary results", The Journal of Thoracic and Cardiovascular Surgery, Aug. 2005, 130(2), 504.31-504.e9.
Das et al., "S100A12 Expression in Thoracic Aortic Aneurysm Is Associated With Increased Risk of Dissection and Perioperative Complications", Journal of the American College of Cardiology, Aug. 2012, 60(8).
Davies et al., "Natural History of Ascending Aortic Aneurysms in the Setting of an Unreplaced Bicuspid Aortic Valve", The Annals of Thoracic Surgery, Apr. 2007, 83(4), 1338-1344.
Davis-Dusenbery et al., "Down-regulation of Kruppel-like Factor-4 (KLF4) by MicroRNA-143/145 Is Critical for Modulation of Vascular Smooth Muscle Cell Phenotype by Transforming Growth Factor-β and Bone Morphogentic Protein 4", The Journal of Biological Chemistry, Jun. 2011, 286, 28097-28110.
Evangelista et al., "Bicuspid Aortic Valve and Aortic Root Disease", Current Cardiology Reports, Jun. 2011, 13(3), 234-241.
Fedak et al., "Clinical and Pathophysiological Implications of a Bicuspid Aortic Valve", Circulation, Aug. 2002, 106, 900-904.

(Continued)

*Primary Examiner* — Daniel E Kolker
*Assistant Examiner* — Aditi Dutt
(74) *Attorney, Agent, or Firm* — BakerHostetler

(57) ABSTRACT

Provided herein are methods for identifying and treating BAV disease and/or aortopathy in a subject, and methods of improving outcome in a subject. The subject may be asymptomatic of BAV disease and/or aortopathy, experiencing symptoms of BAV disease and/or aortopathy, have BAV disease and/or aortopathy, or be a blood relative of an individual having BAV disease and/or aortopathy. Levels of sRAGE in the subject's biological sample are determined, compared to a control biological sample, and used as an indicator for the presence and severity of BAV disease and/or aortopathies, a tool to screen family members, and an indicator of the proper surgical or treatment regimens.

24 Claims, 16 Drawing Sheets

(56) References Cited

OTHER PUBLICATIONS

Fedak et al., "Vascular matrix remodeling in patients with bicuspid aortic valve malformations: implication for aortic dilatation", J Thorac Cardiovacular Surgery, 2003, 126, 797-806.

Friedman et al., "Bicuspid aortic valve: clinical approach and scientific review of a common clinical entity", Expert Review of Cardiovascular Therapy, Jan. 2014, 6(2), 235-248.

Hiratzka et al., "A Report of the American College of Cardiology Foundation/American Heart Association Task Force on Practice Guidelines, American Association for Thoracic Surgery, American College of Radiology, Amercian Stroke Association, Society of Cardiovascular Anesthesiologist, Society for Cardiovacular Angiography and Interventions, Societing of Interventional Radiology, Society of Thoracic Surgeons, and Society for Vascular Medicine", J Am Coll Cardiol, 2010, 55(14), e27-e129.

Hofmann Bowman et al., "S100A12 Mediates Aortic Wall Remodeling and Aortic Aneurysm", Circulation Research, Jan. 2010, 106, 145-154.

Ikonomidis et al., "Aortic Dilatation With Bicuspid Aortic Valves: Cusp Fusion Correlates to Matrix Metalloproteinases and Inhibitors", The Annals of Thoracic Surgery, Feb. 2012, 93(2), 457-465.

Ikonomidis et al., "Plasma biomarkers for distinguishing etiological subtypes of thoracic aortic aneurysm disease", J Thorac Cardiovasc Surg., 2013, 145(5) 1326-1333.

Kang et al., "MicroRNA regulation of smooth muscle gene expression and phenotype", Current Opinion in Hematology, May 2012, 19(3), 224-231.

Lemaire et al., "Matrix metalloproteinases in ascending aortic aneurysms: Bicuspid versus trileaflet aortic valves", Journal of Surgical Research, Jan. 2005, 123(1), 40-48.

Lewin et al., "The Bicuspid Aortic Valve", Circulation, 2005, 111, 832-834.

Lindsay et al., "Lessons on the pathogenesis of aneurysm from heritable conditions", Nature, May 2011, 473(7347), 308-316.

Mautner et al., "Clinical factors useful in predicting aortic valve structure in patients >40 years of age with isolated valvular aortic stenosis", The American Journal of Cardiology, Jul. 1993, 72(2), 194-198.

Michelena et al. "Incidence of aortic complications in patents with bicuspid aortic valves", The Journal of American Medical Association, 2011, 306(10), 1104-1112.

Pacini et al., "Incidence, Etiology, Histologic Findings, and Course of Thoracic Inflammatory Aortopathies", The Annals of Thoracic Surgery, Nov. 2008, 86(5), 1518-1523.

Parish et al., "Aortic size in acute type A dissection: Implication for preventative ascending aortic replacement", Eur J of Cardio-Thoracic Surgery, 2009, 35(6), 941-946.

Parolari et al., "Biological features of thoracic aortic dieseases. Where are we now, where are we heading to: established and emerging biomarkers and molecular pathways", European Journal of Cardio-Thoracic Surgery, Jul. 2013, 44(1), 9-23.

Pisano et al., "Histological and genetic studies in patients with bicuspid aortic valve and ascending aorta complications", Interactive Cardiovascular and Thoracic Surgery, 2011, 14(2012) 300-306.

Rajamannan et al., "Bicuspid aortic valve disease: the role of oxidative stress in Lrp5 bone formation", Cardiovacular Pathology, May-Jun. 2011, 20(3), 168-176.

Ramasamy et al., "Advanced glycation end produces and RAGE: a common thread in aging, diabetes, neurodegeneration, and inflammation", Glycobiology, 2005, 15(7), 16R-28R.

Rangrez et al., "miR-143 and miR-145: Molecular Keys to Switch the Phenotype of Vascular Smooth Muscle Cells", Circulation: Cardiovascular Genetics, 2011, 4, 197-205.

Roberts et al., "Comparision of Valve Structure, Valve Weight, and Severity of the Valve Obstruction in 1849 Patients Having Isolated Aortic Valve Replacement for Aortic Valve Stenosis (with or without Associated Aortic Regurgitation) Studied at 3 Different Medical Centers in 2 Different Time Periods", Circulation, 2005, 112, 3919-3929.

Sarkar et al., "Reasons to Investigate the Soluble Receptor for Adanced Glycation End-Product (sRAGE) Pathway in Aortic Disease", Aorta Journal, 2013, 1(3), 210-217.

Schmidt et al., "The biology of the receptor for advanced glycation end products and its ligands", Biochimica et Biophysica Acta (BBA)—Molecular Cell Research, Dec. 2000, 1498(2-3), 99-111.

Siu et al., "Bicuspid aortic valve disease", Journal of the American College of Cardiology, Jun. 2010, 55(25), 2789-2800.

Tanaka et al., "Diagnostic Value of Cardiac CT in the Evaluation of Bicuspid Aortic Stenosis: Comparison With Echocardiography and Operative Findings", American Journal of Roentgenology, Oct. 2010, 195(4), 895-899.

Wittwer et al., "Methodological and preanalytical evaluation of a RAGE immunoassay", Anticancer Res., 2012, 32(5) 2075-2078.

Yan et al., "Glycation, Inflammation and RAGE", Circulation Research, Dec. 2003, 93, 1159-1169.

Yang et al., "Association between sRAGE, esRAGE levels and vascular inflammation: Analysis with $^{18}$F-fluorodeoxyglucose positron emission tomography", Atherosclerosis, Feb. 2012, 220(2), 402-406.

Zegdi et al., "Detecting aortic valve bicuspidy in patients with severe aortic valve stenosis: high diagnostic accuracy of colour Doppler transoesophageal echocardiography", Interactive Cardiovascular and Thoracic Surgery, Jan. 2013, 16(1), 16-20.

* cited by examiner

METHODS FOR DIAGNOSING AND
TREATING BICUSPID AORTIC VALVE
AND/OR AORTOPATHIES

CROSS REFERENCE TO RELATED APPLICATION

This application is a National Stage Application filed under 35 U.S.C. § 371 of International Application No. PCT/US2014/040662, filed Jun. 3, 2014, which claims the benefit of U.S. Provisional Application No. 61/831,067 filed Jun. 4, 2013, the contents of each of these applications are incorporated herein by reference in their entirety.

FIELD OF THE INVENTION

The disclosed methods relate generally to diagnosing and treating Bicuspid Aortic Valve disease and/or aortopathies using sRAGE levels.

BACKGROUND OF THE INVENTION

With an estimated frequency of 1-2% in the population, Bicuspid Aortic Valve (BAV) is the most common cardiac congenital anomaly in the United States. BAV patients have frequent and premature occurrence of valvular and vascular diseases and the occurrence of life-threatening cardiac events, such as ascending thoracic aortic aneurysm (TAA) and dissection (TAD), and significant valvular dysfunction, such as aortic stenosis (AS), endocarditis, and aortic insufficiency (AI), among others. It has been estimated that between 30% and 50% of patients with BAV will require surgical intervention at some point in their life for valvulopathy, aortopathy, or both.

The current American College of Cardiology (ACC)/American Heart Association (AHA) guidelines recommend replacing the ascending aorta if it is more than 5.5 cm in patients with normal tricuspid aortic valve (also referred to herein as "trileaflet aortic valve") (TAV). Prophylactic surgical repair of the dilated aorta (more than 4.5 cm) is more aggressively recommended for patients with BAV. However, the optimal timing of aortic surgery in TAA patients remains uncertain for both BAV and trileaflet aortic valve (TAV) patients. Studies have shown that more than 60% of patients with acute aortic dissection presented with aortic diameters<5.5 cm. Current surgical guidelines for ascending aortic aneurysm repair (>5.5 cm) would, therefore, fail to prevent the majority of acute aortic dissections seen in these studies. Although aortic diameter, expansion rate, ratio of aortic area/diameter to body weight/surface are the current indications for elective surgical intervention, they are imperfect predictors of aortic dissection and rupture, especially for BAV patients. Even with the more aggressive guidelines that have been adopted for BAV patients, over 20% of patients would not have qualified for preventive aortic replacement. Also of concern is the common development of subsequent ascending aortopathies in patients who have had previous aortic valve replacement for BAV in the near or remote past.

Screening for BAV is dependent on echocardiography and other imaging techniques. BAV is identified via routine echocardiography only in a subgroup of BAV patients— echocardiographic identification can be challenging in severe stenosis and after cusp fusion secondary to inflammation. For these reasons the distinction between TAV and BAV is often difficult in cases of advanced valvulopathy. The use of computed tomography (CT) scan allows for more sensitive measurements in advanced cases of valve degeneration. Currently, no existing diagnostic modality allows an assessment of risk for the subsequent development of aortopathy.

The current mainstay of diagnosis of BAV is echocardiography (transthoracic or transoesophageal) which can provide a definitive diagnosis in the majority of patients. When images are adequate, echocardiography can reach 92% sensitivity and 96% specificity. In the presence of aortic valve calcification, sensitivity and specificity drop to 67% and 69%. Higher diagnostic accuracy has been reported in a relatively small sample population using color Doppler transesophageal echocardiography (TEE), a method that may be poorly tolerated, especially in frail patients. Due to the natural history of BAV, which can lead to heavily calcified stenotic valves, the utility of echocardiography can be extremely limited. Furthermore, echocardiography is not able to fully quantify the extent of any aortopathy (whether proximal or distal). Because of these limitations, cardiac MRI and CT need to be used to augment the diagnostic process.

Thus, there is a need for a diagnostic method for identifying BAV disease and/or aortopathies in an individual. The invention is directed to these and other important needs.

SUMMARY OF THE INVENTION

Provided herein are methods of identifying BAV disease and/or aortopathy in a subject comprising, determining the level of sRAGE in a biological sample of the subject, and comparing the level of sRAGE in the subject's biological sample to the level of sRAGE in a control biological sample, wherein an increased level of sRAGE in the biological sample of the subject relative to the level of sRAGE in the control biological sample is indicative of the subject having BAV disease and/or aortopathies.

Disclosed herein are methods of treating BAV disease and/or aortopathy in a subject. The methods comprise determining the level of sRAGE in a biological sample of the subject, comparing the level of sRAGE in the subject's biological sample to the level of sRAGE in a control biological sample, wherein an increased level of sRAGE in the biological sample of the subject, relative to the level of sRAGE in the control biological sample, is indicative of the subject having BAV disease and/or aortopathies; and treating the subject for BAV disease and/or aortopathy if the level of sRAGE in the biological sample of the subject is increased relative to the level of sRAGE in the control biological sample.

Also provided herein are methods for treating a subject who: 1) is asymptomatic of BAV disease and/or aortopathy; 2) is experiencing symptoms of BAV disease and/or aortopathy; 3) has BAV disease and/or aortopathy; or 4) is a blood relative of an individual having BAV disease and/or aortopathy. The methods comprise determining the level of sRAGE in a biological sample from the subject, comparing the level of sRAGE in the subject's biological sample to the level of sRAGE in a control biological sample, and treating said subject if the level of sRAGE in the biological sample of the subject is increased relative to the level of sRAGE in the control biological sample. For example, treating said subject if the subject has a sRAGE level greater than, for example, about 681 pg/mL.

The general description and the following detailed description are exemplary and explanatory only and are not restrictive of the invention, as defined in the appended claims. Other aspects of the present invention will be apparent to those skilled in the art in view of the detailed description as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods disclosed. In the drawings:

FIGS. 2A-2F, represent comparisons of sRAGE plasma concentrations in BAV patients compared to TAV patients. A) sRAGE quantification of TAV (n=61) and BAV (n=74) patients. Dots represent values (pg/ml) from each patient±SEM. B) sRAGE quantification ROC curve. C) Sensitivity, specificity, and likelihood ratio (LR) for a cut-off of sRAGE concentration 966 pg/ml. D) sRAGE values in TAV (n=27) and BAV (n=40) patients meeting the criteria for surgical intervention (ascending aorta diameter<4.5 cm). E) sRAGE ROC curve relative to panel D. F) Sensitivity, specificity, and LR for a cut-off of sRAGE concentration of 766 pg/ml.

FIGS. 4A-4C, represent: A) sRAGE quantification in plasma samples of BAV patients undergoing AV replacement/repair only with ascending aorta diameter<4.5 cm (BAV AVR, n=30) and BAV patients undergoing AVR combined with ascending aorta procedure (aortoplasty or replacement, BAVAVRAA, n=30) and ascending aorta diameter>4.5 cm (representing the 2010 American College of Cardiology Foundation/American Heart Association guidelines for ascending aorta replacement when concomitant AVR procedure is required); B) Linear correlation between sRAGE plasma quantification and patient's ascending aorta diameter ($p=0.51$, $R^2=0.0005$); and C) ratio between ascending aorta diameter/BSA ($p=0.42$, $R^2=0.07$).

FIGS. 5A-5B, represents sRAGE level distribution in slow and fast progressors. A) sRAGE distribution according to the morphology of the valve (TAV, BAV) the type of surgery performed (AVR or AVR/AA) and the patient's age (younger or older than 60, <-yr, >60 yr). B) BAV patient discrimination in slow progressors vs. fast progressors based on sRAGE plasma values distribution.

FIGS. 6A-6C, represent: A) Ascending aorta diameter measurement by CT-scan (cm), age, and sRAGE concentration (pg/ml) detected in the plasma of patients #1-7; B) Graphs representing sRAGE values (bars), proteoglycan deposition (scored from 0 to +3; triangles) and elastin fragmentation (scored from 0 to −3; squares); and C) Representative images of Modified Movat's Pentachrome staining performed on OCT section of ascending aorta tissues excised from patients #1-7. Media layer. 40× magnification.

FIGS. 8A-8B, represent A) western blot and B) graph of plasma sRAGE, tissue, RAGE, and HMGB1.

FIGS. 9A-9D, is a comparison of the proximal ascending aorta and sRAGE levels in BAV and TAV patients (including surgical and non surgical patients). FIG. 9A depicts a histology analysis (Modified Movat Pentachrome and Verhoeff-Van Gieson staining) of the proximal ascending aorta in both dilated and non-dilated TAV and BAV patients. Analysis was performed on controls (TAV-C), and aneurysmal tricuspid (TAV-TAA), non-dilated bicuspid (BAV-ND), and aneurysmal bicuspid (BAV-TAA) patients. 63× magnification. FIG. 9B depicts sRAGE levels in plasma samples of BAV (n=74) and TAV (n=55) patients (both groups with ascending aorta diameter lower than 5.5 cm). Dots represent values (pg/mL) from each patient±SEM. FIG. 9C represents sRAGE plasma quantification ROC curve. FIG. 9D is a table summarizing sensitivity, specificity, Positive Predictive Value (PPV), Negative Predictive Value (NPV), and Likelihood Ratio (LR) for a cut off of sRAGE plasma concentration equal to 774 pg/ml.

FIGS. 10A-10B, depicts an analysis of sRAGE levels in BAV and TAV patients based upon age and gender. FIG. 10A is a univariate analysis of sRAGE quantification in plasma samples of BAV (n=74) and TAV (n=61) patients divided by gender. Dots represent values (pg/mL) from each patient±SEM. Comparisons were made between male and female in the entire patient population, then intra-group (TAV or BAV) and inter group (TAV vs BAV). Only comparisons that reach statistically significant differences are shown in the figure ($p<0.05$). FIG. 10B represents a linear correlation between sRAGE plasma quantification and patient's age ($p=0.1$, $R^2=0.2$).

FIGS. 12A-12E, depicts an analysis of sRAGE plasma levels in BAV patients who underwent aortic valve replacement (AVR) due to aortic stenosis (AS) or aortic insufficiency (AI) (n=32) and those who presented ascending aorta dilatation (ascending aorta diameter>4.5 cm) concomitantly to AS or AI (n=42). Comparison was made between sRAGE quantification in plasma samples of BAV patients undergoing AVR only (BAV AVR, n=32) and BAV patients undergoing AVR combined with an ascending aorta procedure (aortoplasty or replacement, BAV AVR/AA, n=42) Dots represent values (pg/mL) from each patient±SEM (FIG. 4A). FIG. 12B is a graph representing the specificity and sensitivity of sRAGE quantification in discriminating BAV patients with only valvular pathology from BAV patients with valvular pathology and ascending aorta and aortic arch dilatation. FIG. 12C is a table summarizing sensitivity, specificity, Positive Predictive Value (PPV), and Negative Predictive Value (NPV) for a cut off of sRAGE plasma concentration equal to 1288 pg/ml. Linear correlation between sRAGE plasma quantification and patient's ascending aorta diameter ($p=0.51$, $R^2=0.007$) (FIG. 12D) and ratio between ascending aorta diameter/body surface area (BSA) ($p=0.42$, $R^2=0.011$) (FIG. 12E).

FIGS. 13A-13B, depicts sRAGE analysis in TAV patients with or without aneurysmal ascending aorta. FIG. 5A represents sRAGE quantification in plasma samples of TAV patients with ascending aorta diameter (AA) lower or higher than 5 cm. Dots represent values (pg/mL) for each patient±SEM. P=0.0496. FIG. 13B represents the linear correlation between ascending aorta diameter and sRAGE values in TAV patients.

FIGS. 14A-14B, depicts sRAGE analysis in BAV patients with or without ascending aorta dilatation. FIG. 14A represents sRAGE quantification in plasma samples of BAV patients with ascending aorta diameter (AA) lower or higher than 4.5 cm. Dots represent values (pg/mL) for each patient±SEM. P=0.0183. FIG. 14B represents the linear correlation between ascending aorta diameter and sRAGE values in BAV patients.

FIGS. 16A-16C, depicts sRAGE analysis in TAV and BAV patients undergoing aortic valve replacement. FIG. 16A, sRAGE quantification in plasma samples of TAV and BAV patients who undergo aortic valve replacement (TAV AVR n=32, BAV AVR n=34). Dots represent values (pg/ml) for each patient±SEM. P=0.0004. FIG. 16B, graph representing specificity and sensitivity of sRAGE quantification in discriminating between TAV and BAV patients affected only by valvular pathology (no aneurysm). FIG. 16C is a table summarizing sensitivity, specificity, Positive Predictive Value (PPV), and Negative Predictive Value (NPV) for a cut off of sRAGE plasma concentration equal to 681.1 pg/ml.

DETAILED DESCRIPTION OF ILLUSTRATIVE EMBODIMENTS

Figure 1:
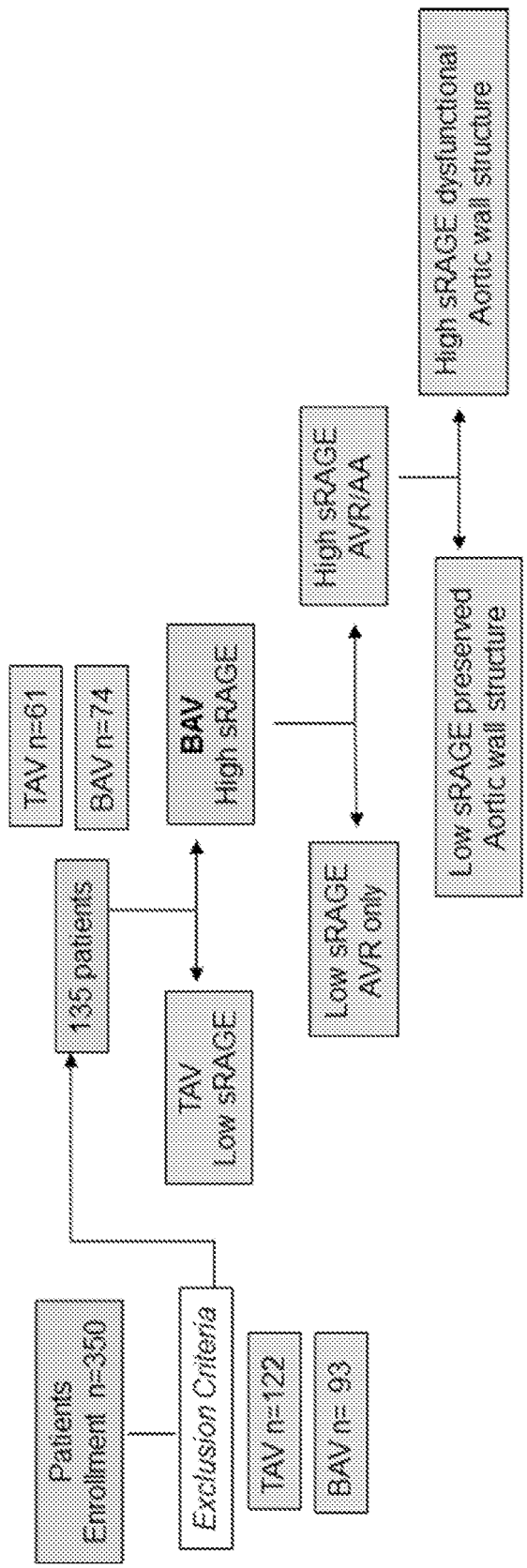
FIG. 1 is a flow chart representing an exemplary study workflow for sRAGE analysis.

The disclosed methods may be understood more readily by reference to the following detailed description taken in connection with the accompanying figures and examples, which form a part of this disclosure. It is to be understood that the disclosed methods are not limited to the specific methods described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination. Further, reference to values stated in ranges include each and every value within that range. All ranges are inclusive and combinable.

Provided herein are methods of identifying BAV disease and/or aortopathy in a subject comprising:
determining the level of sRAGE in a biological sample of the subject; and
comparing the level of sRAGE in the subject's biological sample to the level of sRAGE in a control biological sample, wherein an increased level of sRAGE in the biological sample of the subject relative to the level of sRAGE in the control biological sample is indicative of the subject having BAV disease and/or aortopathies.

Provided herein are methods of treating BAV disease and/or aortopathy in a subject comprising:
determining the level of sRAGE in a biological sample of the subject,
comparing the level of sRAGE in the subject's biological sample to the level of sRAGE in a control biological sample, wherein an increased level of sRAGE in the biological sample of the subject relative to the level of sRAGE in the control biological sample is indicative of the subject having BAV disease and/or aortopathies; and
treating the subject for BAV disease and/or aortopathy if the level of sRAGE in the biological sample of the subject is increased relative to the level of sRAGE in the control biological sample.

As used herein, the term "TAV" refers to tricuspid aortic valve (also referred to has trileaflet aortic valve), which is used to described the normal anatomy of the Aortic Valve (between left ventricle and aorta), in opposition to the congenital abnormality of Bicuspid Aortic Valve "BAV," or another congenital abnormality.

As used herein, the term "BAV" refers to Bicuspid Aortic Valve. It is known by those of skill in the art that BAV is a cardiac congenital anomaly, in which two of the aortic valvular leaflets fuse, resulting in a valve that is "bicuspid" as opposed to the normal "tricuspid." As used herein the term BAV refers to any anatomical configuration in which two cusps are fused, irrespectively of the type of fusion. BAV can exist in isolation, but is often associated with other congenital cardiac lesions. The most frequent associated finding is dilation of the proximal ascending aorta secondary to abnormalities of the aortic media. Changes in the aortic media are present independent of whether the valve is functionally normal, stenotic, or incompetent. For this reason, BAV disease is considered a disease of both the valve and the aorta. Thus, BAV disease includes dysfunction of the tract of the aorta, including the ascending aorta, aortic arch, descending aorta, and abdominal aorta. BAV is associated with frequent and premature occurrence of life-threatening cardiac events, such as ascending aortic aneurysm and dissection, and significant valvular dysfunction, such as aortic stenosis (AS) and aortic insufficiency (AI).

As used herein, the term "BAV disease" includes both valvular and vascular pathologies associated with the detection of BAV. "BAV disease" and "BAV syndrome" encompass both of these pathologies and are used interchangeably herein.

As used herein, the terms "aortopathies" and "aortopathy" refer to any pathological condition of the aorta (for example dilatation, aneurysm, dissection, coarctation or simply dysfunction) whether determined by genetic diseases or having a sporadic onset. BAV disease can be a type of aortopathy.

As used herein, the term "subject" refers to any animal, in particular mammals. Thus, the methods are applicable to human and nonhuman animals. In some aspects of the invention, the methods can be used with humans. In other aspects of the disclosed methods, the subject is a blood relative of an individual having BAV disease and/or an aortopathy. As used herein, the term "blood relative" refers to one related by blood, such as those individuals that share a common ancestor, for example, a son, a daughter, a mother, a father, a grandmother, or grandfather. In other aspects of the invention, the methods can be used with rodents, for example, mice. In yet other aspects of the invention, the methods can be used with non-human mammals, for example, domestic animals such as pigs, horses, or cows. As used herein, the terms "subject," "patient," and "individual" are used interchangeably.

As used herein, the term "RAGE" refers to Receptor for Advanced Glycation Endproducts. It is known by those of skill in the art that RAGE is a multi-ligand member of the immunoglobulin superfamily of cell surface molecules. RAGE functions as a receptor for Advanced Glycation Endproducts (AGEs), the products of nonenzymatic glycation and oxidation of proteins/lipids. RAGE also serves as a signal transduction receptor for proinflammatory S100/calgranulins and amphoterin and amyloid-β-peptide and β-sheet fibrils.

As used herein, the term "sRAGE" refers to soluble RAGE. In addition to the cellular full length receptor, 15 different RAGE mRNA variants have been identified encoding for truncated proteins with different biological properties. The soluble RAGE forms (sRAGE) include the endogenous secretory RAGE (esRAGE) and the proteolytically cleaved form (sRAGE) shed into the circulation by the action of metalloproteinases. Both esRAGE and sRAGE have been shown to act as decoys by binding ligands and counteract the activation of RAGE mediated intracellular pathways.

As used herein, the term "biological sample" refers to any biological specimen taken from a subject. Biological samples for use in the claimed methods include any sample, now known or later identified, that contains sRAGE, including, but not limited to, tissue, blood, plasma, urine, feces, skin, hair, or any combination therein. Thus, for example, in some aspects of the invention, the biological sample is blood.

As used herein, the term "determining the level of sRAGE in a biological sample of the subject" refers to quantifying the amount of sRAGE in any of the above listed biological samples. The sRAGE level can be nucleic acid that encodes RAGE or sRAGE, such as DNA, RNA, and mRNA, with or without the promoter and regulatory elements of the gene, and the RAGE or sRAGE protein or peptides. sRAGE levels can be determined by any one of a variety of techniques known to those of skill in the art. These techniques include, but are not limited to, spectroscopy, fluorescence assays, colorimetric assays, polymerase chain reaction ("PCR"), enzyme-linked immunosorbent assay ("ELISA"), radiolabelling, labeling with tags, real time PCR (RTPCR), immunoprecipitation, Western blotting, or any combination thereof.

The level of sRAGE in a biological sample of the subject is compared to the level of sRAGE in a control biological sample. As used herein, the term "control biological sample" refers to a biological sample from one or more subjects that do not have BAV disease and/or an aortopathy. Thus, "control" refers to non-BAV populations. In some embodiments, control biological samples are TAV. Preferably, the control biological sample excludes those patients having heart defects such as unicuspid aortic valve (UAV) and quadricuspid aortic valve (QAV). Thus, the level of sRAGE in the control biological sample is indicative of an individual that does not have BAV disease and/or an aortopathy. The level of sRAGE in a control biological sample can be obtained through a variety of sources, including, but not limited to, searching public databases or scientific/medical literature, or it can be determined by measuring the sRAGE levels from an individual who does not have BAV disease and/or aortopathies (control) at the time of analyzing the subject. In a preferred embodiment, the control and subject population are determined within each study based on that study's inclusion and exclusion criteria. Inclusion and exclusion criteria are defined based on the current scientific knowledge on the disease (which is the object of the study) and on the tested molecule.

As used herein, the phrase "the level of sRAGE in a biological sample of the subject is compared to the level of sRAGE in a control biological sample" means analyzing the difference in sRAGE levels between the samples.

In certain embodiments, an sRAGE level of the biological sample that is ±15% of the control biological sample is indicative of an individual without BAV.

For example, in other aspects of the invention, a sRAGE level of less than about 681 pg/mL is indicative of an individual without BAV, i.e. an individual having TAV with no aortopathies, whereas a level of sRAGE above about 681 pg/mL is indicative of a BAV and/or aortopathy. Thus, by comparing the sRAGE levels between the subject's biological sample and that of a control biological sample, BAV disease and/or aortopathies can be readily identified.

In some aspects, the subject is asymptomatic of BAV disease and/or aortopathy. A defective valve can function for years without causing symptoms. Thus, although BAV disease is present at birth, it is possible that the subject will be asymptomatic their entire life or that diagnosis will not occur until adulthood. Identification of sRAGE in an asymptomatic subject can be used to implement protocols that will improve the long-term prognosis of the subject. For example, such protocols can include changes in the subject's lifestyle (diet and exercise) and/or health management (routine heart monitoring, medication, and the like).

The disclosed methods can be used to identify a blood relative having BAV. Thus, identification of BAV disease allows for the routine screening of BAV family members providing early identification, surveillance, and treatment of that population.

In other aspects of the disclosed methods, the subject exhibits symptoms of BAV disease and/or another aortopathy. Rarely, the disease is so severe at birth that the baby develops congestive heart failure early in life. More commonly, patients will have a history of having a childhood murmur and symptoms will develop in mid-life as the valve ages. Symptoms of BAV disease and/or another aortopathy include, but are not limited to, a heart murmur during childhood or adult life (e.g., not severe BAV disease), chest pain or pressure (e.g., BAV stenosis), shortness of breath during exertion/intolerance to exercise (e.g., BAV stenosis/insufficiency), fatigue (e.g., BAV stenosis/insufficiency), dizziness (e.g., BAV stenosis), fainting (e.g., BAV stenosis), palpitations (e.g., BAV stenosis), congestive heart failure (e.g., BAV stenosis), or any combination thereof.

BAV disease progression can occur in a number of ways. For example, calcium deposits on and around the leaflets eventually cause the valve to stiffen and narrow, a condition known as stenosis. As stenosis develops, the heart must pump increasingly harder to force the blood through the valve. Symptoms of a stenotic valve include chest pain, shortness of breath and dizziness or fainting caused by inadequate blood flow to the brain. If the bicuspid valve does not close completely, blood can flow backwards into the heart (referred to as regurgitation or aortic valve insufficiency). The heart must then pump that same blood out again, causing strain on the heart's lower left chamber, the left ventricle. Over time, the ventricle will dilate, or overexpand. The main symptom of aortic valve regurgitation is shortness of breath during exertion, like walking up stairs. As the disease progresses, these symptoms start occurring more frequently, even without exercise.

Aortopathies can occur in different ways. For example, aneurysm disease is usually a silent but indolent process because it often grows slowly and usually without symptoms, making this disease difficult to detect unless an imaging study has been performed for other reasons. Some aneurysms start small and stay small, although others expand over time. How quickly an aortic aneurysm grows is difficult to predict. As a thoracic aortic aneurysm grows, symptoms may occur such as tenderness or pain in the chest, back pain, hoarseness, cough, and shortness of breath. Most people with aortic aneurysms do not have symptoms unless a tear (dissection) or rupture has occurred, in which case symptoms will include sharp, sudden pain in the upper back that radiates downward, chest, jaw, neck or arm pain, and difficulty breathing. Furthermore a dysfunctional structure (aortopathy) of the ascending aorta may lead to dissection and rupture even in the absence of dilatation.

The disclosed methods comprise treating the subject for BAV disease and/or aortopathy if the level of sRAGE in the biological sample of the subject is increased relative to the level of sRAGE in the control biological sample. As used herein, "treatment" refers to the care given to a subject in order to reduce, eliminate, and/or prevent the severity and/or frequency of BAV symptoms, and to improve or remediate the damage caused by BAV. Treatment includes, but is not limited to, imaging, increased frequency of monitoring by a health care professional, patient and family education, administering a therapeutic compound, life style changes, dietary changes, surgery, or any combination thereof.

Methods of treatment can be based, in part, upon the level of sRAGE in the subject's biological sample. For example, the higher the level of sRAGE above a control level, the more indicative of the need for treatment. Thus, the claimed methods can be used to identify subjects who require a more aggressive treatment based upon an elevated sRAGE level.

In some aspects of the disclosed methods, the subject is treated for BAV disease and/or aortopathy if the level of sRAGE in the biological sample of the subject is at least any value between about 600 pg/ml and 2500 pg/ml. For example, in some aspects of the invention, the level of sRAGE can be at least 600 pg/mL. In other aspects, the level of sRAGE can be at least 650 pg/mL. In other aspects, the level of sRAGE can be at least 700 pg/mL. In other aspects, the level of sRAGE can be at least 750 pg/mL. In other aspects, the level of sRAGE can be at least 800 pg/mL. In other aspects, the level of sRAGE can be at least 850 pg/mL. In other aspects, the level of sRAGE can be at least 900 pg/mL. In other aspects, the level of sRAGE can be at least 950 pg/mL. In other aspects, the level of sRAGE can be at least 1000 pg/mL. In other aspects, the level of sRAGE can be at least 1050 pg/mL. In other aspects, the level of sRAGE can be at least 1100 pg/mL. In other aspects, the level of sRAGE can be at least 1150 pg/mL. In other aspects, the level of sRAGE can be at least 1200 pg/mL. In other aspects, the level of sRAGE can be at least 1250 pg/mL. In other aspects, the level of sRAGE can be at least 1300 pg/mL. In other aspects, the level of sRAGE can be at least 1350 pg/mL. In other aspects, the level of sRAGE can be at least 1400 pg/mL. In other aspects, the level of sRAGE can be at least 1450 pg/mL. In other aspects, the level of sRAGE can be at least 1500 pg/mL. In other aspects, the level of sRAGE can be at least 1550 pg/mL. In other aspects, the level of sRAGE can be at least 1600 pg/mL. In other aspects, the level of sRAGE can be at least 1650 pg/mL. In other aspects, the level of sRAGE can be at least 1700 pg/mL. In other aspects, the level of sRAGE can be at least 1750 pg/mL. In other aspects, the level of sRAGE can be at least 1800 pg/mL. In other aspects, the level of sRAGE can be at least 1850 pg/mL. In other aspects, the level of sRAGE can be at least 1900 pg/mL. In other aspects, the level of sRAGE can be at least 1950 pg/mL. In other aspects, the level of sRAGE can be at least 2000 pg/mL. In other aspects, the level of sRAGE can be at least 2050 pg/mL. In other aspects, the level of sRAGE can be at least 2100 pg/mL. In other aspects, the level of sRAGE can be at least 2150 pg/mL. In other aspects, the level of sRAGE can be at least 2200 pg/mL. In other aspects, the level of sRAGE can be at least 2250 pg/mL. In other aspects, the level of sRAGE can be at least 2300 pg/mL. In other aspects, the level of sRAGE can be at least 2350 pg/mL. In other aspects, the level of sRAGE can be at least 2400 pg/mL. In other aspects, the level of sRAGE can be at least 2450 pg/mL. In other aspects, the level of sRAGE can be at least 2500 pg/mL. In a preferred aspect of the disclosed methods, the level of sRAGE in the biological sample of the subject is at least about 681 pg/mL. In another aspect, the level of sRAGE in the biological sample of the subject is at least about 1765 pg/mL. In yet another preferred aspect, the level of sRAGE in the biological sample of the subject is at least about 2209 pg/mL.

In other aspects of the disclosed methods, the subject is treated for BAV disease and/or aortopathy if the level of sRAGE in the biological sample of the subject is at least 15% greater than the level of sRAGE in the control biological sample. In some aspects, the level of sRAGE in the biological sample of the subject is at least about 30% greater than the level of sRAGE in the control biological sample. In some aspects, the level of sRAGE in the biological sample of the subject is at least about 40% greater than the level of sRAGE in the control biological sample. In some aspects, the level of sRAGE in the biological sample of the subject is at least about 65% greater than the level of sRAGE in the control biological sample. In some aspects, the level of sRAGE in the biological sample of the subject is at least about 90% greater than the level of sRAGE in the control biological sample. In some aspects, the level of sRAGE in the biological sample of the subject is at least about 115% greater than the level of sRAGE in the control biological sample. In some aspects, the level of sRAGE in the biological sample of the subject is at least about 140% greater than the level of sRAGE in the control biological sample. In some aspects, the level of sRAGE in the biological sample of the subject is at least about 165% greater than the level of sRAGE in the control biological sample. In some aspects, the level of sRAGE in the biological sample of the subject is at least about 190% greater than the level of sRAGE in the control biological sample. In some aspects, the level of sRAGE in the biological sample of the subject is at least about 215% greater than the level of sRAGE in the control biological sample. In some aspects, the level of sRAGE in the biological sample of the subject is at least about 240% greater than the level of sRAGE in the control biological sample. In some aspects, the level of sRAGE in the biological sample of the subject is at least about 265% greater than the level of sRAGE in the control biological sample. In some aspects, the level of sRAGE in the biological sample of the subject is at least about 290% greater than the level of sRAGE in the control biological sample. In some aspects, the level of sRAGE in the biological sample of the subject is at least about 300% greater than the level of sRAGE in the control biological sample.

In other aspects of the disclosed methods, the level of sRAGE in the biological sample of the subject is at least about 15% to about 300% greater than the level of sRAGE in the control biological sample. In other aspects of the disclosed methods, the level of sRAGE in the biological sample of the subject is at least about 15% to about 250% greater than the level of sRAGE in the control biological sample. In other aspects of the disclosed methods, the level of sRAGE in the biological sample of the subject is at least about 15% to about 200% greater than the level of sRAGE in the control biological sample. In other aspects of the disclosed methods, the level of sRAGE in the biological sample of the subject is at least about 15% to about 150% greater than the level of sRAGE in the control biological sample. In other aspects of the disclosed methods, the level of sRAGE in the biological sample of the subject is at least about 15% to about 100% greater than the level of sRAGE in the control biological sample. In other aspects of the disclosed methods, the level of sRAGE in the biological sample of the subject is at least about 15% to about 50% greater than the level of sRAGE in the control biological sample. In other aspects of the disclosed methods, the level of sRAGE in the biological sample of the subject is at least about 15% to about 45% greater than the level of sRAGE in the control biological sample. In other aspects of the disclosed methods, the level of sRAGE in the biological sample of the subject is at least about 15% to about 40% greater than the level of sRAGE in the control biological sample. In other aspects of the disclosed methods, the level of sRAGE in the biological sample of the subject is at least about 15% to about 35% greater than the level of sRAGE in the control biological sample. In other aspects of the disclosed methods, the level of sRAGE in the biological sample of the subject is at least about 15% to about 30% greater than the level of sRAGE in the control biological sample. In other aspects of the disclosed methods, the level of sRAGE in the biological sample of the subject is at least about 15% to about 25% greater than the level of sRAGE in the control biological sample. In other aspects of the disclosed methods, the level of sRAGE in the biological sample of the subject is at least about 15% to about 20% greater than the level of sRAGE in the control biological sample.

In other aspects of the disclosed methods, the level of sRAGE in the biological sample of the subject is at least about 150% to about 300% greater than the level of sRAGE in the control biological sample. In other aspects of the disclosed methods, the level of sRAGE in the biological sample of the subject is at least about 175% to about 300% greater than the level of sRAGE in the control biological sample. In other aspects of the disclosed methods, the level of sRAGE in the biological sample of the subject is at least about 200% to about 300% greater than the level of sRAGE in the control biological sample. In other aspects of the disclosed methods, the level of sRAGE in the biological sample of the subject is at least about 225% to about 300% greater than the level of sRAGE in the control biological sample. In other aspects of the disclosed methods, the level of sRAGE in the biological sample of the subject is at least about 250% to about 300% greater than the level of sRAGE in the control biological sample. In other aspects of the disclosed methods, the level of sRAGE in the biological sample of the subject is at least about 275% to about 300% greater than the level of sRAGE in the control biological sample. In other aspects of the disclosed methods, the level of sRAGE in the biological sample of the subject is at least about 290% to about 300% greater than the level of sRAGE in the control biological sample.

As used herein, the term "about," when referring to sRAGE levels, is meant to encompass variations of ±20% or less, variations of 10% or less, variations of ±5% or less, variations of ±1% or less, variations of ±0.5% or less, or variations of ±0.1% or less from the specified value.

In some aspects of the disclosed methods, treatment comprises surgery. For example, in some embodiments, the treatment comprises aortic valve replacement when the level of sRAGE in the biological sample is increased relative to the level of sRAGE in the control biological sample. In other aspects of the disclosed methods, the treatment comprises ascending aortic replacement when the level of sRAGE in the biological sample is increased relative to the level of sRAGE in the control biological sample. In other aspects of the disclosed methods, the treatment comprises a combination of aortic valve replacement and ascending aorta surgery when the level of sRAGE in the biological sample is increased relative to the level of sRAGE in the control biological sample. Ascending aortic surgery includes a large spectrum of surgical interventions. The type of technical procedures depends, in part, on the status of the patient, and would be known to one having ordinary skill in the art.

In some embodiments, treatment comprises imaging the aortic valve of the subject if the level of sRAGE in the subject's biological sample is increased relative to the level of sRAGE in the control biological sample. Imaging techniques are well known to one of ordinary skill in the art and include, but are not limited to, echocardiography (transthoracic or transesophageal), color Doppler transesophageal echocardiography, cardiac magnetic resonance imaging, computerized tomography, or a combination thereof. Thus, for example, in some aspects of the claimed methods, the subject's aortic valve can be imaged by echocardiography after it is determined that the level of sRAGE in the subject's biological sample is increased relative to the level of sRAGE in the normal biological sample. In other aspects of the claimed methods, the subject's aortic valve can be imaged by color Doppler transesophageal echocardiography after determining that the sRAGE levels are increased. In other aspects of the claimed methods, the subject's aortic valve can be imaged by cardiac magnetic resonance imaging after it is determined that sRAGE levels are increased. In other aspects, computerized tomography can be used to image the subject's aortic valve after it is determined that he has increased sRAGE levels. In yet other aspects, echocardiography and computerized tomography can be used to image the subject's aortic valve. In other aspects, a combination of imaging techniques can be employed. It would be obvious to one of ordinary skill in the art what the best imaging technique, or combination thereof, would be for the individual patient.

In other aspects, the treatment comprises administering a therapeutic compound to the patient in an amount effective to reduce symptoms of BAV disease and/or the aortopathy. For example, in some embodiments of the invention, the therapeutic compound is a cholesterol-reducing compound, a blood pressure-lowering compound, prophylactic antibiotic, diuretic compound, or any combination thereof. Pharmacological treatment can also comprise targeting AGE accumulation by, for example, administering ACE inhibitors, aminoguanidine (AG), pyridoxamine, or other other carbonyl trapping agents, dietary antioxidants (such as vitamin C, vitamin E (α-tocopherol), benfotiamine, (a synthetic S-acyl derivative of thiamine), agents having anti-inflammatory, anti-oxidant, and/or metal chelation properties, or any combination thereof.

The disclosed methods provide a tool for the risk-stratification of patients into "fast" and "slow" progression. Without intent to be bound by theory, this distinction will allow changes in clinical care in several non-mutually exclusive ways, for example, the frequency of monitoring both valve and aortic values. Serial follow-up evaluations are important for early recognition of potential complications (valve insufficiency, valve stenosis, progressive aortic root dilation) and the prevention of possible bacterial endocarditis.

Clinical care for BAV patients (and their first degree relative) differs from TAV patients, even more if a BAV patient is at high risk of adverse aortic event. Notably, care extends to non-cardiac care. For non-cardiac surgical procedures, for example, preoperative cardiac evaluation may be appropriate, particularly for patients with aortic stenosis or insufficiency. Additionally, because hypercholesterolemia and other coronary artery disease risk factors may accelerate the sclerosis and deterioration of a congenitally bicuspid aortic valve, a heart-healthy diet is recommended for all patients, not only those with recognized risk factors. The disclosed methods enable the implementation of treatments sooner and more effectively.

Other life-style changes that are the result of the disclosed methods may be related to physical activities. Patients who develop valve insufficiency or stenosis from a congenitally bicuspid aortic valve may require restrictions from strenuous competitive sports. Patients with aortic valve insufficiency should avoid strenuous isometric activity, such as weight lifting, rope climbing, and pull-ups. This is particularly important in the case of ascending aortopathies (even more so for aortopathies that are not associated with aortic dilation, such as an exemplary patient population described herein: normal diameter, but high sRAGE levels)

Patient and family education should emphasize the fairly benign course for the child with bicuspid aortic valve. Older children and adolescents should begin to be made aware of the accelerated aging processes (ie, progressive stenosis), with particular attention to coronary risk factors. The importance of bicuspid aortic valve as a potential substrate for infective endocarditis should be emphasized.

The claimed methods can be performed at any one of a number of times during a subject's lifetime. For example, the methods can be performed as part of a general health screen of the subject, such as when the subject is having a physical examination or checkup at his or her doctor. Alternatively, the methods can be performed prior to surgery, so as to guide the doctors in the proper surgical procedure. In some aspects of the invention, the methods can be performed prior to aortic valve replacement. In other aspects of the invention, the methods can be performed prior to ascending aorta replacement.

Also provided herein are methods of treating a subject who:

1) is asymptomatic of BAV disease and/or another aortopathy;

2) is experiencing symptoms of BAV disease and/or another aortopathy;

3) has BAV disease and/or another aortopathy; or 4) is a blood relative of an individual having BAV disease and/or another aortopathy;

comprising determining the level of sRAGE in a biological sample from the subject comparing the level of sRAGE in the subject's biological sample to the level of sRAGE in a control biological sample, and treating said subject if the level of sRAGE in the biological sample of the subject is increased relative to the level of sRAGE in the control biological sample.

As used herein, the term "outcome" refers to the health or prognosis of a subject. The claimed methods can be used to improve a subject's health through, for example, life style changes and health management. Identifying a BAV disease and/or another aortopathy in a subject who is asymptomatic and unaware of its existence will enable that subject to seek proper medical advice regarding how to properly manage and control the disease, including surgery and/or imaging. This may also result in a change of diet and exercise to prevent further complications. The claimed methods can also be used to improve a subject's prognosis. For example, the methods can be used for a subject experiencing symptoms of, or having, BAV disease and/or another aortopathy, allowing doctors to perform the proper course of treatment, such as surgery and/or imaging.

The claimed methods can also be used as a screening technique for family members of an individual having BAV and/or another aortopathy. For example, due to the hereditary nature of BAV and other aortopathies, upon identification of one affected family member, other family members can be screened to determine whether they too have BAV and/or another aortopathy.

Surgical procedures used in the treatment or prevention of BAV disease and/or another aortopathies are well known to one or ordinary skill in the art. Surgical procedures within the claimed methods include, but are not limited to, aortic valve replacement, ascending aorta surgery, or a combination thereof. Thus, in some aspects of the invention, the subject can undergo aortic valve replacement if the subject has a sRAGE level greater than about 681 pg/mL. In other aspects, the subject can undergo ascending aorta surgery if the subject has a sRAGE level greater than about 681 pg/mL. In other aspects of the invention, the subject can undergo aortic valve replacement and ascending aorta surgery if the subject has a sRAGE level greater than about 681 pg/mL.

As discussed in greater detail herein, imaging techniques for use in the claimed methods include, but are not limited to, echocardiography (transthoracic or transesophageal), color Doppler transesophageal echocardiography, cardiac magnetic resonance imaging, computerized tomography, or a combination thereof.

EXAMPLES

Example 1

Analysis of sRAGE Levels: Surgical Population

Study Population

A retrospective study was performed on a total of 338 patients enrolled at the University of Pennsylvania according to the approved IRB protocol #809349 (FIG. 1). All patients included in this study have been followed for aortic valve diseases (stenosis or insufficiency) and/or enlargement of the ascending aorta and reached the criteria for surgical intervention. Blood was taken before surgery and all patients provided written informed consent. Surgical patients were divided in two groups, according to the morphology of the aortic valve assessed by transesophageal echocardiography (TTE), computed tomography (CT scan) or both, and confirmed by intra-operatory observation. Exclusion criteria were: genetic disease associated with TAA, connective tissue disease, chronic inflammatory disease, previous myocardial infarction, severe heart failure (NYHAIII+, IV), endocarditis, active cancer. A total of 135 patients met the inclusion criteria, n=74 with BAV and n=61 with TAV.

Among them, 32 BAV and 33 TAV underwent aortic valve replacement without aortoplasty (BAVAVR). 42 BAV and 29 TAV underwent aortic valve repair or replacement combined with an ascending aorta surgery (repair or replacement) (BAVAVR/AA or TAVAVR/AA). A detailed description the patients' demographics is summarized in Table 1 and 2.

TABLE 1

Patient Enrollment

|  | TAV | BAV |
|---|---|---|
| Enrollment n = 338 | 178 | 160 |
| Exclusion Criteria: |  |  |
| Syndromic TAA/ConnettiveTissue Diseases | 7 (3.9%) | 0 |
| Other heart defect | 0 | 4 (2.5%) |
| Thoracic Aortic Dissection | 10 (5.6%) | 0 |
| Endocarditis | 0 | 6 (3.75) |
| Chronic Disease | 25 (14.0%) | 14 (8.75%) |
| Inflammatory Disease | 19 (10.7%) | 12 (7.5%) |
| Previous MI | 13 (7.3%) | 11 (6.9%) |
| Heart Failure (NYHA III+/IV) | 18 (10.1%) | 14 (8.8%) |
| History of Cancer | 34 (19.1%) | 25 (15.6%) |
| Included n = 135 | 61 (34.3%) | 74 (46.3%) |

TABLE 2

Patient Demographics

| Demographics | TAV n = 61 | BAV n = 74 | p |
|---|---|---|---|
| Demographic and Clinical Details: total n = 135 surgical patients | | | |
| Age | 64.4 ± 11 | 55.5 ± 13 | <0.001 |
| Male subjects | 71% | 64.4% | 0.164 |
| Smokers | 19.4% | 43% | 0.004 |
| Diabetes | 13.2% | 5.3% | 0.312 |
| Hypertension | 43.40% | 31.6% | 0.024 |
| Coronary artery disease | 22.6% | 5.4% | 0.003 |
| Hyperlipidemia | 43.4% | 27.7% | 0.024 |
| Diagnosis and Type of Surgery | | | |
| Aortic Valve Insufficiency | 68.9% | 70.3% | 0.351 |
| Aortic Valve Stenosis | 34.4% | 74.3% | 0.002 |
| Aortic Valve Repair/Replacement | 55.73% | 43.24% | 0.025 |
| AVR and AA Repair/Replacement | 44.3% | 56.8% | 0.080 |

Aortic Tissue Collection

Ascending aorta was excised from BAV patients undergoing aortic valve replacement combined with ascending aorta surgery. A small fragment of ascending aorta was also obtained from patients with TAV undergoing aortic valve replacement only.

Immunohistochemistry of OCT Sections

Fresh ascending aorta tissues were collected during surgery, fixed in formalin and embedded in OCT. Hematoxylin & Eosin and Modified Movat's Pentachrome staining were performed on 6 µm sections by the MCRC histology core at the University of Pennsylvania. Black stain indicates nuclei and elastic fibers; yellow stain indicates collagen fibers; blue stain indicates proteoglycans and glycosaminoglycans; red indicates muscular tissue.

sRAGE Quantification

Blood was collected prior to surgery from the patients and processed to obtain serum and plasma, then stored at −80° C. until the assay was performed. Plasma analysis for sRAGE level was conducted using ELISA kits (R&D Systems).

Study Design sRAGE levels were analyzed in two ways: at first comparisons were made between all BAV and TAV patients then between BAV and TAV patients with ascending aorta diameter≤4.5 cm. Linear regression was used to determine the relationship between sRAGE values and age, gender, diagnosis of CAD and diabetes and presence of common risks factor for cardiovascular disease (hypertension, hyperlipidemia, smoking) Second, comparisons were made, within the BAV group, (and within the TAV group) between patients undergoing AVR surgery only and patients undergoing AVR and ascending aorta surgery (AVR/AA). Linear regression was calculated between sRAGE values and ascending aorta diameter and ratio between ascending aorta diameter/body surface area (BSA). BSA was calculated using the Mosteller formula.

Statistical Analysis

The data were analyzed using SPSS software (version 19.1; IBM/SPSS, Chicago, Ill.) and SAS (version 9.2). Continuous variables are expressed as mean±standard error (SEM). Comparisons of continuous variables between groups were performed with the nonparametric (Mann-Whitney U test) tests to adjust for abnormalities in the distribution of variables. Multivariate General Linear Model ANOVA was used to evaluate the relationship of factors and their interactions with the level of sRAGE. Differences were considered statistically significant at values of $p<0.05$. To determine the specificity and sensitivity of sRAGE quantification, area under the receiver operating characteristic curves (AUC of ROC curves) was calculated using statistical software GraphPad Prism 5. Regression analyses were performed using SAS (proc logistic) with goodness of fit testing according to the methods of Hosmer and Lemeshow.

Results

Figure 2:
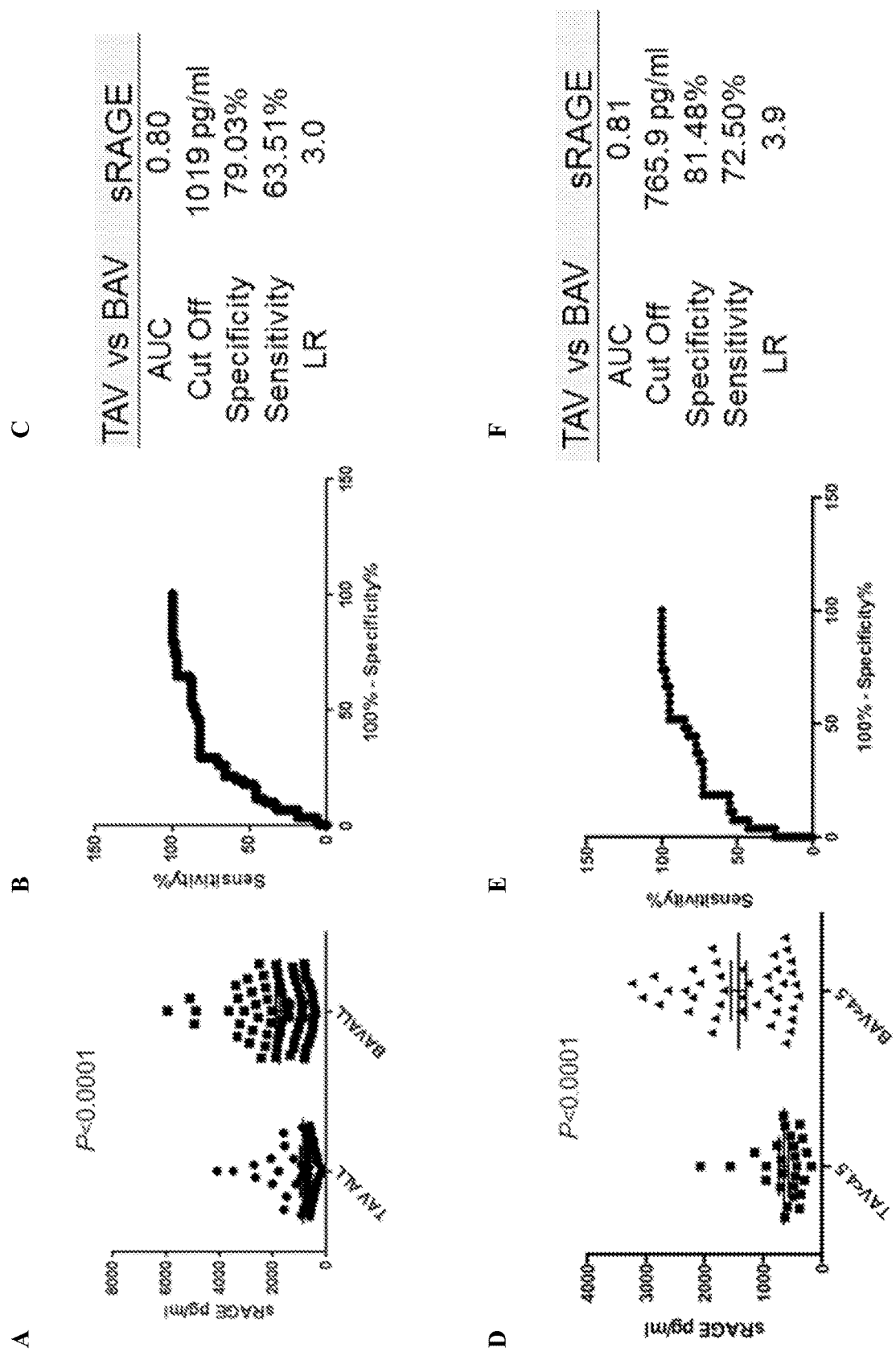
FIG. 2, comprising

Circulating Plasma Levels of sRAGE Identify Bicuspid Aortic Valve Patients in a Surgical Patient Population Independently of Age, Gender, and Common Cardiovascular Co-Morbidities A total of 135 surgical patients (Table 1-2) matching the inclusion criteria were analyzed (FIG. 1). Plasma levels of sRAGE in all BAV (n=74) and TAV (n=61) patients was first examined. As shown in FIG. 2A sRAGE mean values are significantly higher in BAV patients (1765±142.9 pg/ml) than in TAV (733.9±49.26 pg/ml) (p<0.0001). Receiver operator characteristic curve (ROC) was performed to determine if plasma levels of sRAGE could discriminate BAV and TAV patients. As shown in (FIGS. 2B-C), a cut-off of sRAGE plasma level equal to 996 pg/ml maximized area under the curve (AUC) values to 0.80 and identifies BAV with 63.5% sensitivity and 79% specificity (FIG. 2C). These patients have concomitant occurrence of aortic valve stenosis/insufficiency and ascending aortic dilation: since the current ACC/AHA guidelines suggest ascending aortic replacement for BAV and TAV patients undergoing AVR if the aortic diameter is greater than 4.5 cm, plasma level of sRAGE in the BAV and TAV subgroups of patients with diameter lower than the parameter suggested by the guidelines was measured. In this sub-analysis of 27 TAV and 40 BAV patients a cutoff of 766 pg/ml maximized area under the curve (AUC) values to 0.81 and identify BAV with 81.5% sensitivity and 72.5% specificity (LR of 3.9) (FIGS. 2C-E).

Figure 3:
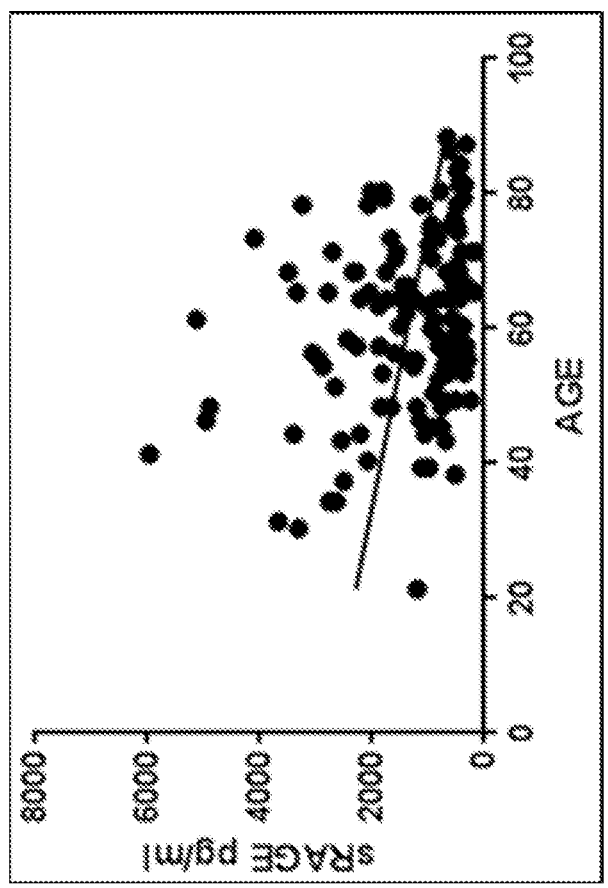
FIG. 3, is a graph representing sRAGE (pg/ml) vs. age of the patient.

As shown in FIG. 3, circulating plasma levels of sRAGE identify Bicuspid Aortic Valve patients in a surgical patient population independently of age.

Figure 4:
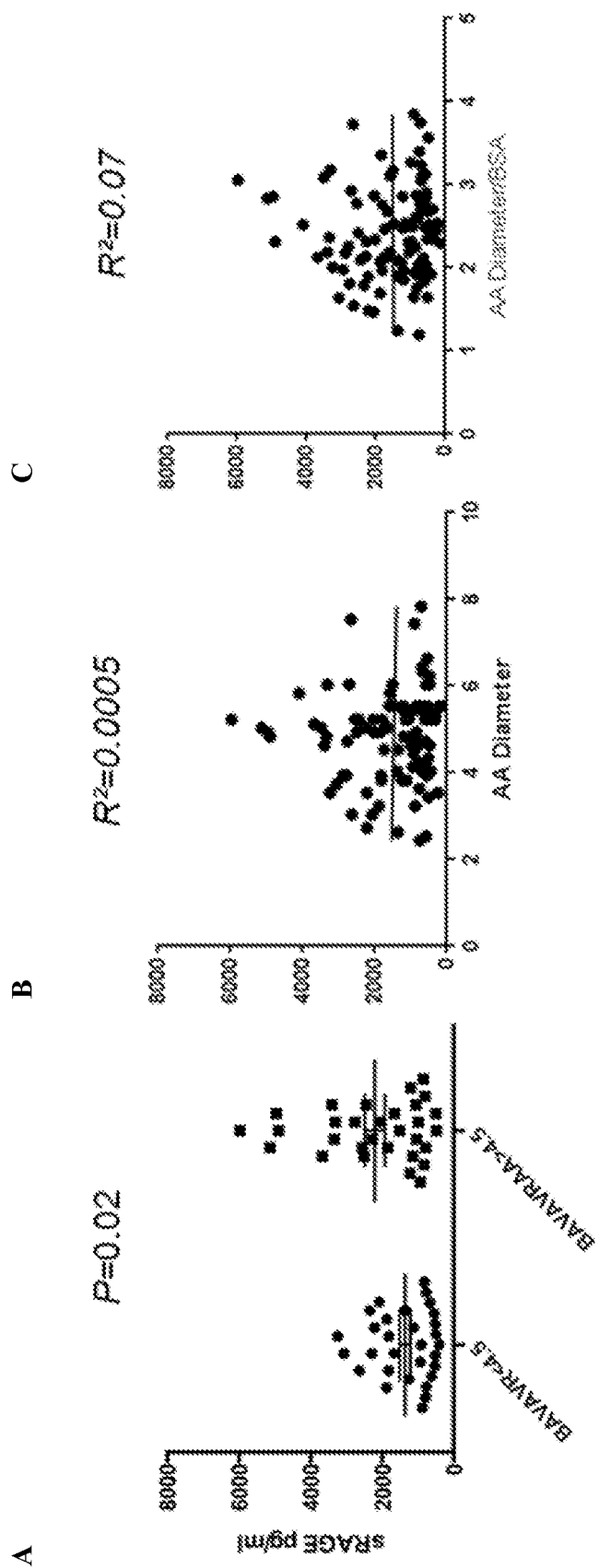
FIG. 4, comprising

As shown in Tables 3 and 4, Multivariate General Linear Model ANOVA was performed to evaluate whether sRAGE was a significant and independent predictor of BAV in the dataset. In addition to the sRAGE values, factors entered into the model were age, gender, coronary artery disease, hypertension, hyperlipidemia, diabetes, history of smoking/ tobacco use, BSA, AI and AS. The model for the overall group showed that the presence of BAV is significantly and independently related to higher levels of sRAGE. Table 4 demonstrates that this relationship is even more pronounced in patients who have an ascending aorta measurement of less than 4.5 cm.

and those who presented ascending aorta dilatation (ascending aneurysm>4.5 cm) concomitantly to AS or AI (n=30). As shown in FIG. 4A BAV patients with only valve pathology (mean ascending aorta diameter equal to 3.7 cm) presented sRAGE plasma values of 1365±150.4 pg/mL while patients who presented aortic valve pathology and aortic dilatation (mean ascending aorta diameter equal to 4.9 cm), show

TABLE 3

Multivariate General Linear Model ANOVA analysis with 134 BAV and TAV Patients

| | | | Unique Method | | | | |
|---|---|---|---|---|---|---|---|
| | | | Sum of Squares | df | Mean Square | F | Sig. |
| sRAGE | Covariates | (Combined) | 6713950.132 | 3 | 2237983.377 | 2.028 | .114 |
| | | Age | 2142198.183 | 1 | 2142198.183 | 1.941 | .166 |
| | | AA Diameter | 3114371.176 | 1 | 3114371.176 | 2.822 | .096 |
| | | BSA | 2598714.955 | 1 | 2598714.955 | 2.355 | .128 |
| | Main Effects | (Combined) | 20729681.835 | 12 | 1727473.486 | 1.565 | .111 |
| | | Valve BAV vs TAV | 8088719.330 | 1 | 8088719.330 | 7.330 | .008 |
| | | AVS | 1429537.527 | 1 | 1429537.527 | 1.295 | .257 |
| | | Gender | 71201.957 | 1 | 71201.957 | .065 | .800 |
| | | Coronary Artery Disease | 10106.454 | 1 | 10106.454 | .009 | .924 |
| | | Diabetes | 733192.763 | 1 | 733192.763 | .664 | .417 |
| | | Smoking | 102709.056 | 1 | 102709.056 | .093 | .761 |
| | | Hyperlipidemia | 401470.698 | 1 | 401470.698 | .364 | .548 |
| | | Hypertension | 537994.370 | 1 | 537994.370 | .488 | .486 |
| | | AVI | 2079775.162 | 4 | 519943.790 | .471 | .757 |
| | Model | | 37314409.094 | 15 | 2487627.273 | 2.254 | .008 |
| | Residual | | 1.302E8 | 118 | 1103520.024 | | |
| | Total | | 1.675E8 | 133 | 1259622.345 | | |

TABLE 4

Multivariate General Linear ANOVA Model with 66 BAV and TAV with AA Diameter <4.5 cm.

| | | Unique Method | | | | |
|---|---|---|---|---|---|---|
| | | Sum of Squares | df | Mean Square | F | Sig. |
| Co-variates | (Combined) | 4268699.952 | 3 | 1422899.984 | 2.817 | .049 |
| | Age | 125978.015 | 1 | 125978.015 | .249 | .620 |
| | AA Diameter | 1781031.101 | 1 | 1781031.101 | 3.526 | .066 |
| | BSA | 1959382.238 | 1 | 1959382.238 | 3.879 | .055 |
| Main Effects | (Combined) | 14892000.604 | 13 | 1145538.508 | 2.268 | .020 |
| | Valve BAV vs TAV | 3914969.522 | 1 | 3914969.522 | 7.750 | .008 |
| | Gender | 583778.871 | 1 | 583778.871 | 1.156 | .288 |
| | Coronary Artery Disease | 227826.147 | 1 | 227826.147 | .451 | .505 |
| | Diabetes | 2272.456 | 1 | 2272.456 | .004 | .947 |
| | Smoking | 1073252.867 | 1 | 1073252.867 | 2.125 | .151 |
| | Hyper-lipidemia | 194980.352 | 1 | 194980.352 | .386 | .537 |
| | Hypertension | 409432.850 | 1 | 409432.850 | .810 | .372 |
| | AVI | 898212.767 | 3 | 299404.256 | .593 | .623 |
| | AVS | 798263.030 | 3 | 266087.677 | .527 | .666 |
| Model | | 18649372.236 | 16 | 1165585.765 | 2.307 | .013 |
| Residual | | 24753496.082 | 49 | 505173.389 | | |
| Total | | 43402868.318 | 65 | 667736.436 | | |

Patients Requiring Ascending Aorta Replacement have Higher sRAGE Level than Patients Requiring AVR Only BAV patients were then divided in two subgroups: those who underwent only aortic valve repair/replacement (AVR) due to severe aortic stenosis (AS) or insufficiency (AI) (n=30) but no ascending aorta dilatation (diameter<4.5 cm), sRAGE levels equal to 2209±278.8 pg/mL (p=0.02). Logistic regression was then performed to test whether sRAGE values were correlated with ascending aorta diameter or the ratio between ascending aorta diameter and body surface area (BSA). As shown in FIG. 4B there is no correlation between sRAGE levels and ascending aorta diameter ($R^2=0.007$, p=0.51) or the ratio between ascending aorta diameter/BSA ($R^2=0.011$, p=0.42).

Figure 5:
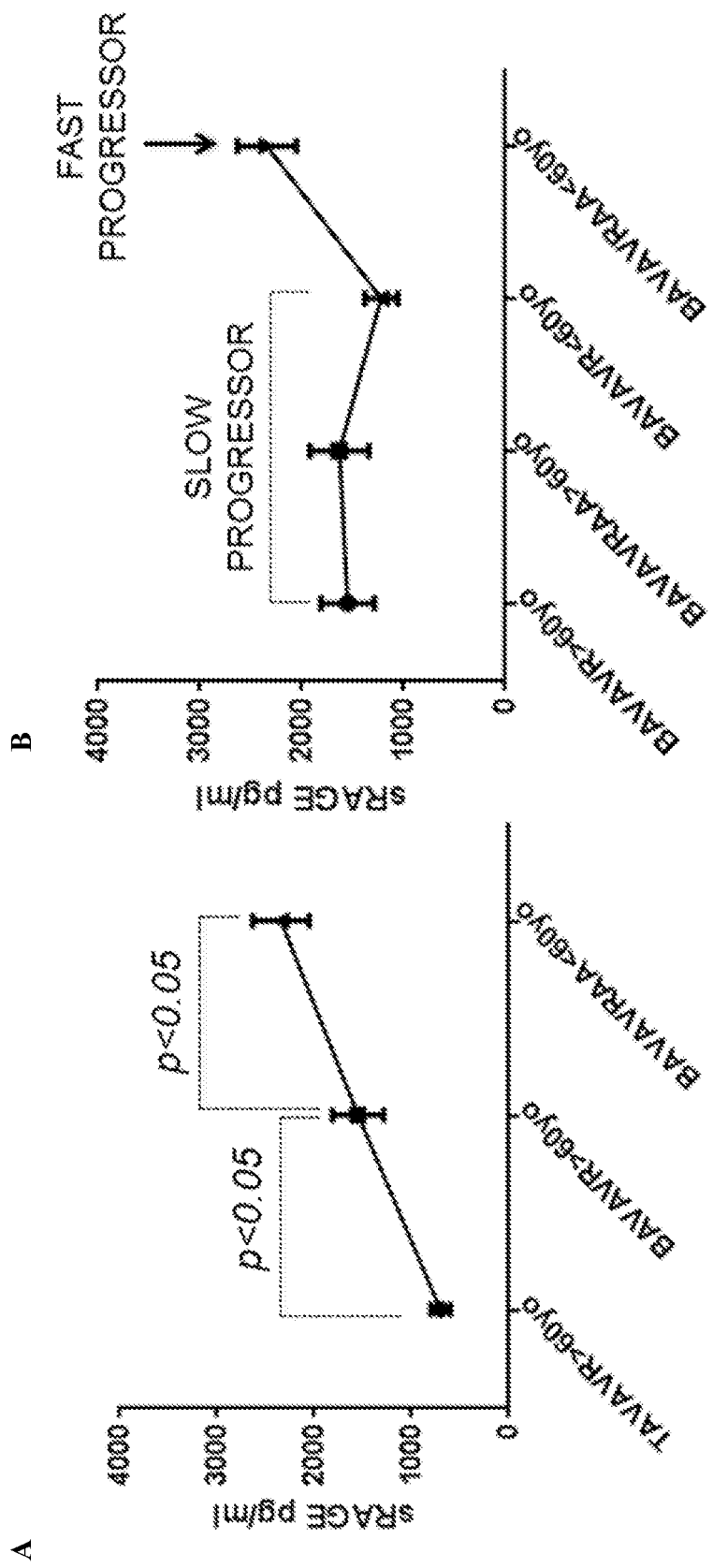
FIG. 5, comprising

Furthermore, BAV patients population was divided into four groups using the age of 60 as an arbitrary cut-off: those under the age of 60 undergoing AVR only, those requiring both AVR and AA under the age of 60, those undergoing AVR only over the age of 60, and those requiring both AVR and AA over the age of 60 (FIG. 5). In the setting of AA development, those patients that required AVR and AA before the age of 60 were considered as "fast progressors", while those requiring AA and AVR or just AVR older than 60 years of age as "slow progressors" (p<0.05) (FIG. 5A). Interestingly, plasma levels of sRAGE in the "fast progressors" group were significantly higher when compared to any of the other group, independently of aortic diameter (FIG. 5B).

Figure 6:
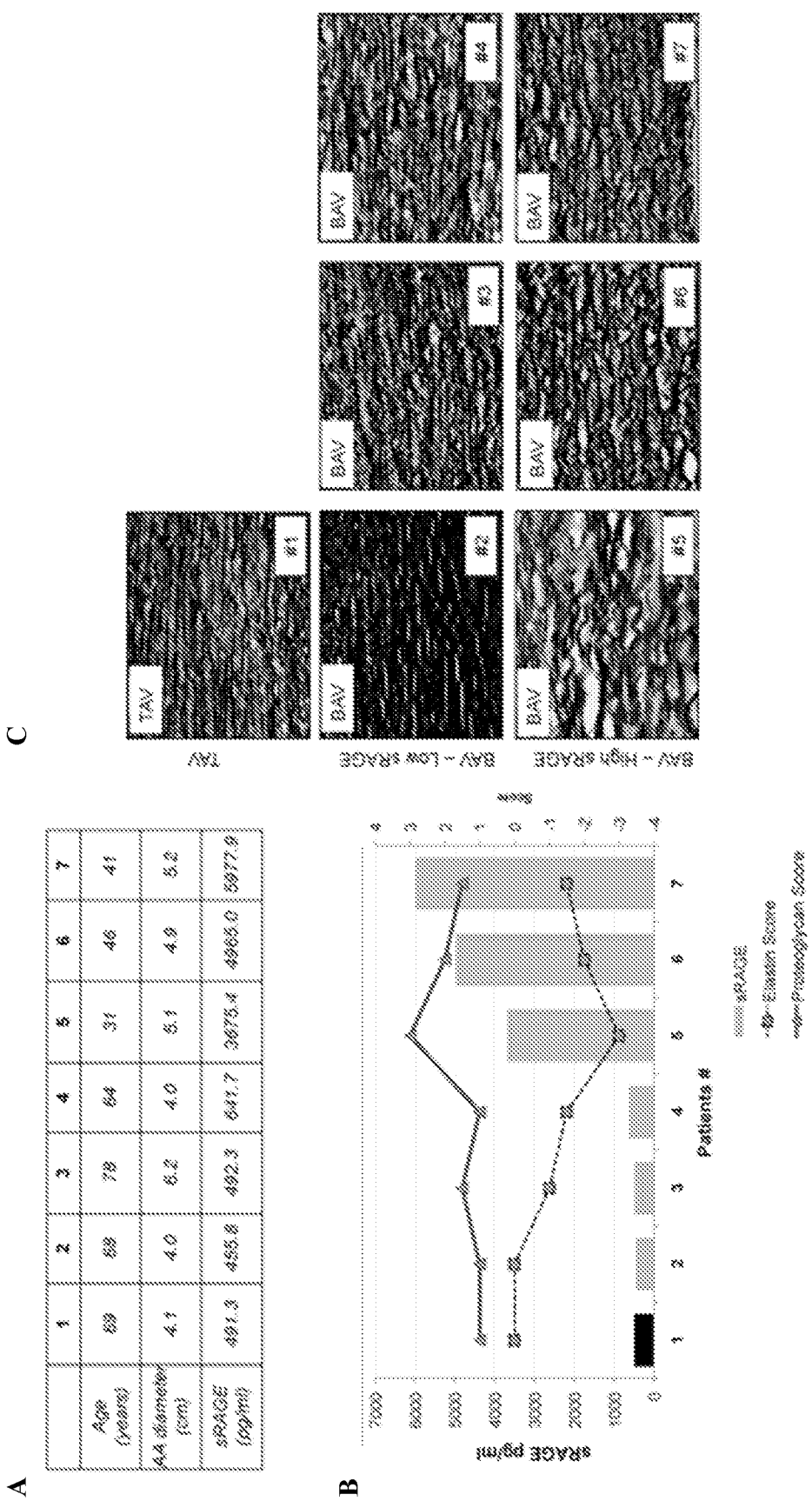
FIG. 6, comprising

Plasma Levels of Soluble sRAGE Correlate with Altered Ascending Aorta Microstructures Ascending aortic tissues were then analyzed for BAV patients using sRAGE values. A subgroup of 6 BAV patients expressing either high or low sRAGE levels were selected and analyzed by a pathologist based on modified Movat Pentachrome staining Age, maximum aortic diameter and soluble sRAGE are indicated in FIG. 6A. Quantification of elastin degradation and proteoglycans deposition show that sRAGE correlate with dysfunctional ascending aortic microstructures (FIGS. 6B and 6C). Control TAV level shows, as expected, low level of sRAGE, normal elastin fiber alignment, and limited proteoglycan deposition. BAV patients with low levels of sRAGE show, despite great variation in the individual ascending aortic diameters, similar elastin and proteoglycan value comparable to the TAV reference. Interestingly, BAV patients with high level of soluble sRAGE show dysfunctional aortic microstructure with elastin fragmentation and proteoglycan deposition regardless of the aortic diameter.

The above results indicate that sRAGE levels are significantly higher in BAV patients compared to TAV and that a cut-off equal to 766 pg/ml is able to identify BAV patients with 82% sensitivity and 69% specificity. Circulating levels of sRAGE can identify BAV patients with higher sensitivity and specificity and independently from the condition of the valve (insufficient, stenotic or heavily calcified).

Furthermore, sRAGE ability to identify BAV patients and BAV associated aortopathies is not affected by the presence of coronary artery disease and diabetes or by common risk factor for cardiovascular diseases (Tables 3 and 4). The availability of a blood-based test to identify BAV disease can allow for routine screens for patients and family members, thus allowing early identification and surveillance with anticipated better compliance.

Commonly used imaging techniques to assess the presence of a BAV do not generally provide information on the risk of aortopathies (either proximal or distal). The data herein indicates that higher levels of sRAGE were detected in BAV patients with aortic valve pathology and ascending aortopathies when compared to BAV patients with only valvular pathologies. No linear correlation has been found between high levels of sRAGE and aortic diameter or aortic diameter/BSA in BAV patients with ascending aneurysm. These results suggest that higher levels of sRAGE may be a marker for the diagnosis of aortic complications in BAV patients with no linear correlation with aortic diameter. In addition, patients requiring both aortic valve replacement and ascending aorta replacement before the age of 60 (fast progressors), have higher sRAGE levels than any other groups in our surgical population (slow progressors) (FIG. 5).

Additionally, the results indicate that, in a subpopulation of BAV patients, sRAGE level directly correlated with altered ascending aorta microstructures. While BAV patients with low sRAGE show an overall organized aortic microstructure, higher levels of sRAGE are associated with elastin degradation and proteoglycan deposition (FIG. 5).

sRAGE Levels in the Plasma Correlate with RAGE and HMGB1 Expression in the Ascending Aorta Tissue To reinforce the concept that higher level of sRAGE correlate with a dysfunctional microstructure of the ascending aorta, RAGE and HMGB1 levels were analyzed in the tissue of a randomly selected patients.

Figure 7:
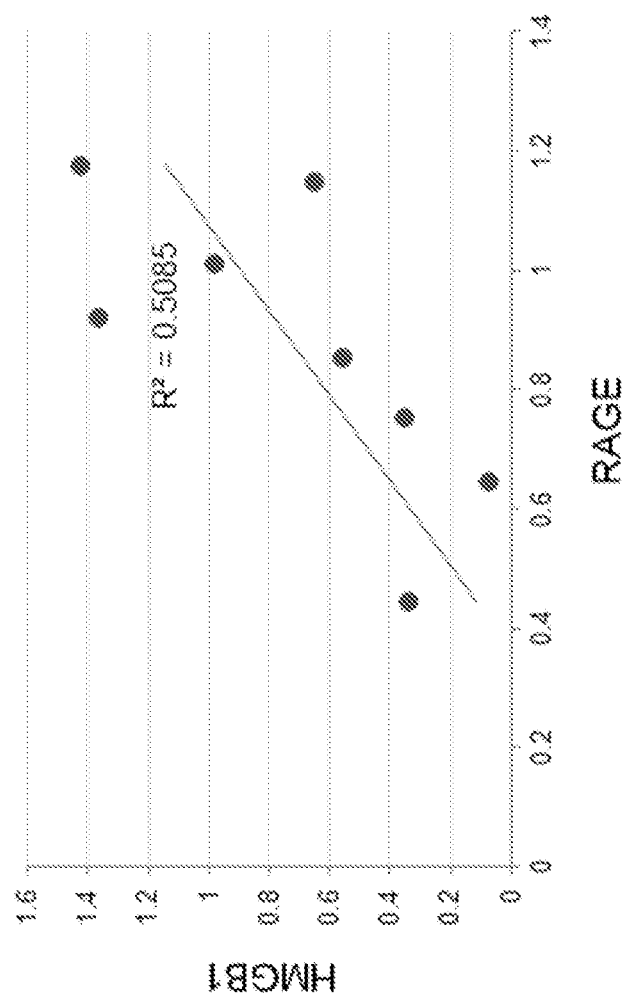
FIG. 7, is a graph representing the linear correlation between tissue levels of RAGE and the tissue level of HMGB1 in human aortic specimens.
Figure 8:
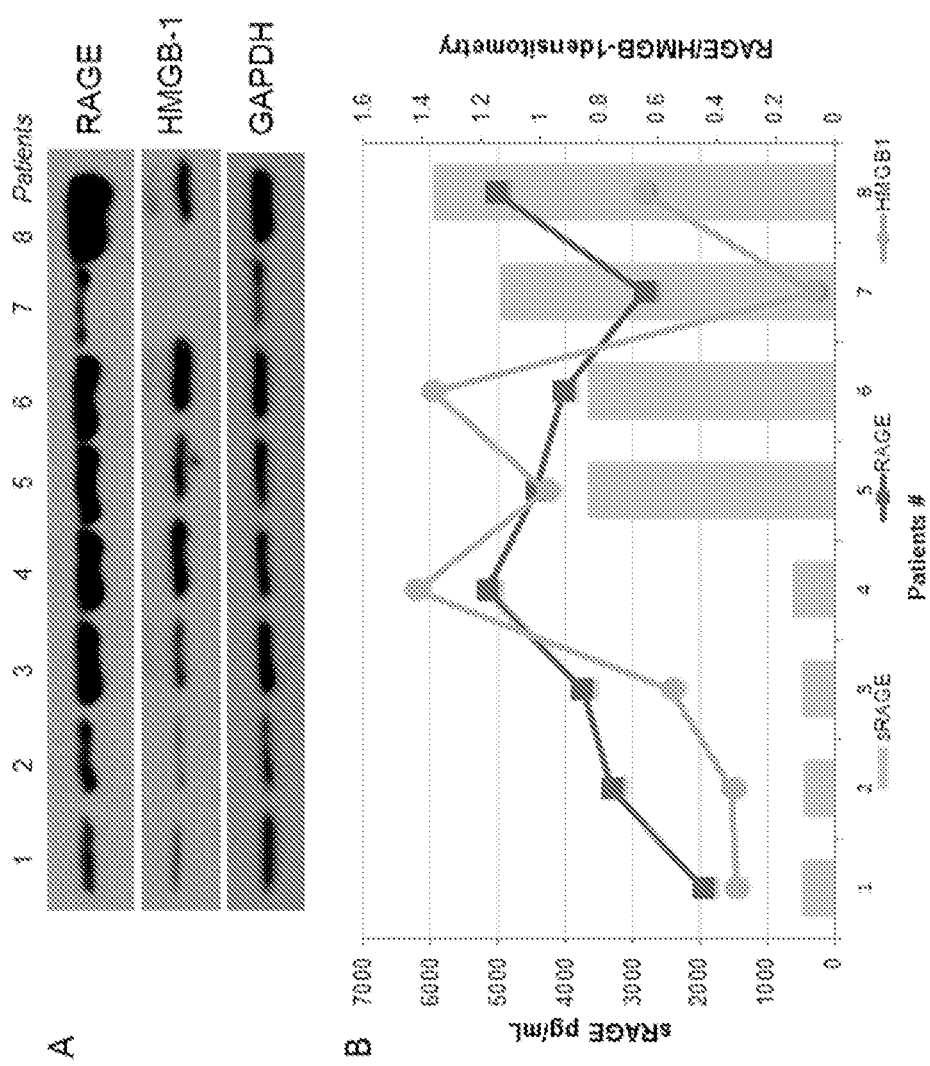
FIG. 8, comprising

To test whether sRAGE levels in the plasma of TAV and BAV patients were dependent on RAGE activation in the ascending aorta of the same patients, the expression of RAGE and its main ligand HMGB-1 were evaluated in the aortic tissue. The expression of RAGE and HMGB-1 was tested by Western blotting using whole aorta tissue extracts of TAV (FIG. 7, pt n=1) and BAV (FIG. 7, pt n=2-8) patients with increasing plasma levels of sRAGE. As shown in FIG. 7 patients with increased levels of sRAGE in the plasma have also increase expression of RAGE and HMGB-1 in the tissue. This result suggests that the activation of RAGE in the tissue by one of its ligand (HMGB1) induces activation of RAGE and the shedding of the receptor into circulating sRAGE.

This data indicates that increased level of sRAGE in the plasma correlates with higher level of RAGE and HMGB-1 in the aortic tissue (FIG. 7) and the presence of a dysfunctional aortic structure (FIG. 6), suggesting that sRAGE levels in the plasma may be used as a marker of the status of aortopathy progression and may be a useful tool in predicting major adverse aortic events.

Example 2

Analysis of sRAGE Levels: Surgical and Non-Surgical Population

Study Population

A retrospective study was performed on a total of 350 patients enrolled at the University of Pennsylvania Hospital according to the approved IRB protocol #809349. All patients included in this study have been followed for aortic valve diseases (stenosis or insufficiency) and/or enlargement of the ascending aorta and reached the criteria for surgical intervention. Blood was taken before surgery and all patients provided written informed consent. Surgical patients were divided in two groups, according to the morphology of the aortic valve assessed by transesophageal echocardiography (TTE), computed tomography (CT scan), or both, and confirmed by intra-operatory observation. Two-hundred fifteen patients were excluded based on the following exclusion criteria: genetic disease associated with TAA, connective tissue disease, chronic inflammatory disease, previous myocardial infarction, severe heart failure (NYHAIII+, IV), endocarditis, active cancer. A total of 135 patients met the inclusion criteria, n=74 with BAV and n=61 with TAV. Among them, 32 BAV and 40 TAV underwent aortic valve replacement without aortoplasty (BAVAVR) and 42 BAV and 8 TAV underwent aortic valve repair or replacement combined with an ascending aorta surgery (repair or replacement) (BAVAVR/AA or TAVAVR/AA). Also included were n=13 patients with no history of cardiovascular diseases as healthy control. A detailed description of the patients' demographics is summarized in Table 5.

TABLE 5

Patients Demographic

| | TAV | BAV | |
|---|---|---|---|
| | N = 61 | N = 74 | p |
| Demographic and Clinical Details | | | |
| Demographics | | | |
| Age | 58.9 ± 20 | 55.8 ± 13 | 0.287 |
| Male subjects | 71% | 61.8% | 0.249 |
| Smokers | 22.7% | 42% | 0.022 |
| Diabetes | 13.2% | 5.3% | 0.114 |
| Hypertension | 43.40% | 31.6% | 0.173 |
| Coronary artery disease | 22.7% | 5.3% | 0.003 |
| Hyperlipidemia | 43.4% | 27.7% | 0.064 |
| Diagnosis and Type of Surgery | | | |
| Aortic Valve Insufficiency | 37.7% | 46.2% | 0.351 |
| Aortic Valve Stenosis | 39.6% | 71.1% | 0.004 |
| Aortic Valve Repair/Replacement | 60.40% | 39.50% | 0.025 |
| AVR and AA Repair/Replacement | 24.02% | 60.50% | 0.080 | sRAGE Quantification

Blood was collected prior to surgery from the patients and processed to obtain serum and plasma, then stored at −80° C. until the assay was performed. Plasma analysis for sRAGE level was conducted using ELISA kits (R&D Systems) and following manufacturer's instructions. Of note, sRAGE has been shown to be highly stable when measured from stored samples and robust to multiple freeze thaw cycles (Wittwer C, Lehner J, Fersching D, Siegele B, Stoetzer O J, Holdenrieder S. Methodological and preanalytical evaluation of a RAGE immunoassay. Anticancer Res. 2012; 32(5):2075-8.).

Study Oversight sRAGE levels were analyzed in two ways: first comparison was made between BAV and TAV patients with ascending aorta diameter≤5.5 cm. Linear regression was calculated between sRAGE values and age, gender, diagnosis of CAD and diabetes and presence of common risks factor for cardiovascular disease (hypertension, hyperlipidemia, smoking) Second, comparisons were made, within the BAV group, (and within the TAV group) between patients undergoing AVR surgery only and patients undergoing AVR and ascending aorta surgery (AVR/AA). Linear regression was calculated between sRAGE values and ascending aorta diameter and ratio between ascending aorta diameter/body surface area (BSA). BSA was calculated using the Mosteller formula.

Statistical Analysis

The data were analyzed using SPSS software (version 21; SPSS) and SAS (version 9.2). Continuous variables were expressed as mean±standard error (SEM). Comparisons of continuous variables between groups were performed with the Student's t test or nonparametric (Mann-Whitney U test) tests as appropriate, depending upon normal distribution. Differences were considered statistically significant at values of $P<0.05$. To determine the specificity and sensitivity of sRAGE quantification, area under the receiver operating characteristic curves (AUC of ROC curves) were calculated using statistical software GraphPad Prism 5. Regression analyses were performed using SAS (proc logistic) with goodness of fit testing according to the methods of Hosmer and Lemeshow.

Figure 9:
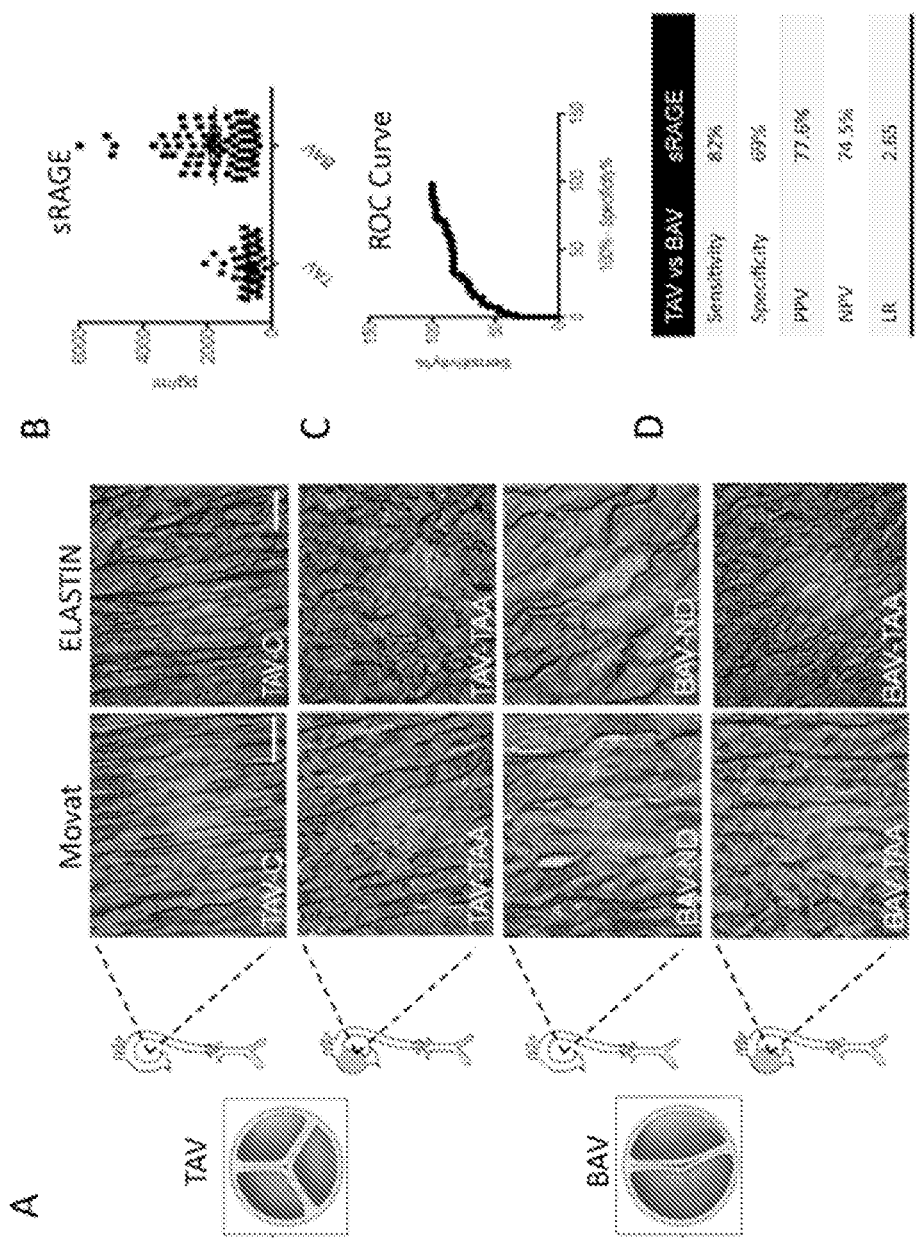
FIG. 9, comprising

Plasma Levels of sRAGE are Significantly Higher in BAV Patients Compared to TAV Patients Plasma levels of sRAGE in BAV (n=74) and TAV (n=55) patients with ascending aorta diameter lower than 5.5 cm were first examined. As shown in FIG. 9B sRAGE mean values are significantly higher in BAV patients (1765±142.9 pg/ml) than in TAV (733.9±49.26 pg/ml) ($p<0.0001$). Receiver operator characteristic curve (ROC) analysis was performed to determine if plasma levels of sRAGE could serve as a biomarker for discriminating BAV and TAV patients. As shown in FIG. 9C, a cut-off of sRAGE plasma level equal to 774 pg/ml maximized area under the curve (AUC) values to 0.82 and identify BAV with 82% sensitivity, 69% specificity, a positive predictive value of 77.63% and negative predictive value of 74.5% (FIG. 9D). Notably, based on recent reports, the identified cut-off offered a specificity and sensitivity higher than the echocardiographic evaluation.

Evaluation of sRAGE Plasma Levels Based Upon Gender and Age

Figure 10:
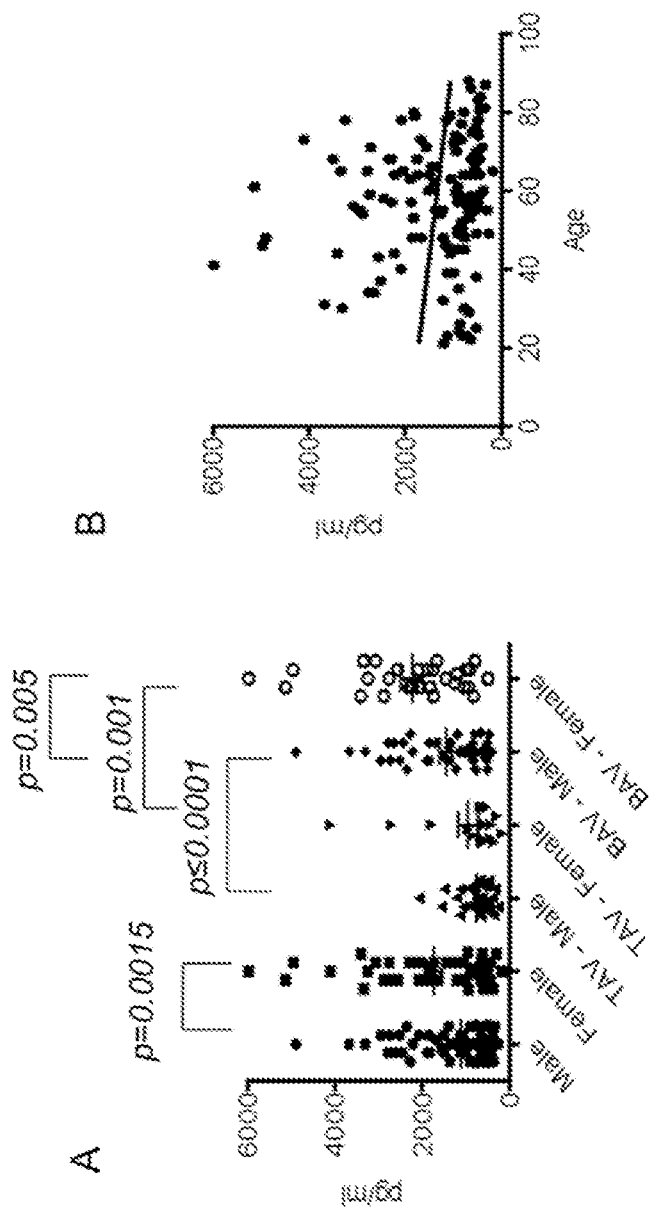
FIG. 10, comprising

Logistic regression was performed to test whether sRAGE plasma levels may be affected by age and gender in our patient population. As shown in FIG. 10B, no significant correlation was found between sRAGE and age in both TAV and BAV patients ($R^2=0.2$, $p=0.1$). Plasma concentrations of sRAGE were significantly higher in the female population ($p=0.0015$). FIG. 10A shows that in the TAV group sRAGE values are not significantly different between male and female. On the contrary, in BAV group sRAGE plasma concentration is significantly higher in female when compared to male ($p=0.005$).

Figure 11:
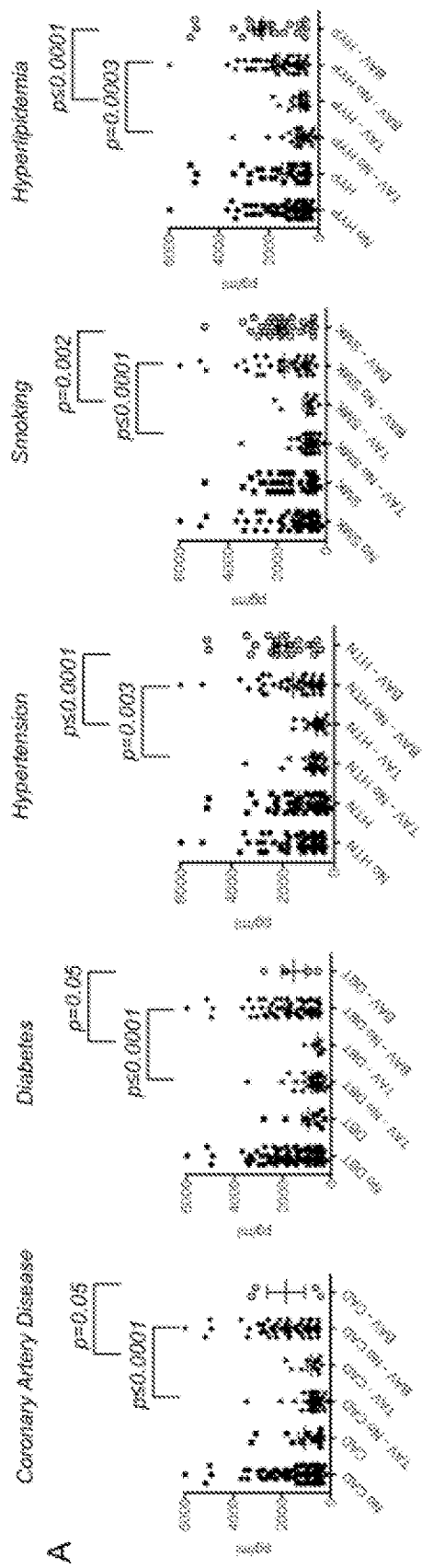
FIG. 11, depicts a univariate analysis of sRAGE quantification in plasma samples of BAV (n=74) and TAV (n=61) patients with or without coronary artery disease, diabetes, hypertension, smoking and hyperlipidemia. Dots represent values (pg/mL) from each patient±SEM. Comparisons were made between presence and absence of the tested condition in the entire patient population, then intra-group (TAV or BAV) and inter group (TAV vs BAV). Only comparisons that reach statistically significant differences are shown in the figure ($p<0.05$).

Effects of Coronary Artery Disease (CAD), Diabetes, Hypertension, Hyperlipidemia and Smoking on sRAGE Plasma Concentration Univariate analysis was performed to test whether the presence of coronary artery disease (CAD), diabetes, hypertension, hyperlipidemia or smoking may affect sRAGE plasma concentration. Comparison between sRAGE values in the different groups was performed at first based on the presence or absence of the tested condition in all patients, then intra-group (within TAV and BAV) and inter-group (TAV versus BAV). sRAGE values are not significantly different in patients with CAD, diabetes, hypertension and hyperlipidemia or smoking when compared to those without these conditions. (FIG. 11) sRAGE values are not significantly different in the TAV patients, with or without CAD, diabetes, hyperlipidemia, hypertension and smoking ($p>0.05$). In BAV patients, sRAGE values are higher in the presence of hyperlipidemia, while are not significantly different in the presence or absence of all the other condition. Analysis between BAV and TAV shows that plasma concentration of sRAGE is significantly higher in the BAV group both in the presence and absence of CAD, diabetes, hypertension, hyperlipidemia and smoking ($p<0.05$). Type of comparison, number of patients/groups and p values are summarized in Table 6.

TABLE 6

Univariate analysis of sRAGE quantification

| | CAD | | DBT | | HTN | | HYP | | SMK | |
|---|---|---|---|---|---|---|---|---|---|---|
| | n Patients | p value | n Patients | p value | n Patients | p value | n Patients | p value | n Patients | p value |
| NO ALL vs YES ALL | 113/15 | 0.32 | 118/10 | 0.24 | 80/48 | 0.78 | 86/42 | 0.33 | 86/42 | 0.18 |
| NO TAV vs YES TAV | 45/11 | 0.92 | 50/6 | 0.25 | 31/25 | 0.15 | 34/22 | 0.56 | 44/12 | 0.96 |
| NO BAV vs YES BAV | 68/4 | 0.91 | 68/4 | 0.7 | 49/23 | 0.08 | 52/20 | 0.03 * | 42/30 | 0.76 |
| NO TAV vs NO BAV | 45/68 | <0.0001 * | 50/68 | <0.0001 * | 31/49 | 0.0027 * | 34/52 | 0.0003 * | 44/42 | <0.0001 * |
| YES TAV vs YES BAV | 11/4 | 0.05 * | 6/4 | 0.05 * | 25/23 | <0.0001 * | 22/20 | <0.0001 * | 12/30 | 0.002 * |

Binary logistic regression was performed to determine multivariate predictors of bicuspid aortic valve in the dataset. Predictors entered into the model were age, sRAGE value, gender, coronary artery disease, hypertension, hyperlipidemia, diabetes, history of smoking/tobacco use. AI and AS were excluded from the model due to selection criteria favoring patients with aortic valve disease in the BAV group—separate sub-models were performed on patients with and without AS. In the overall cohort, predictors of BAV were sRAGE value (OR 1.001, 95% CI 1.001-1.002) and smoking (OR 3.0, 95% CI 1.2-7.6). The interaction term between sRAGE value and smoking was not significant (p=0.09). The model had a c-statistic 0.82 and a Hosmer and Lemeshow Goodness of Fit p=0.4, indicating good predictive accuracy and fit. Using the empirically determined sRAGE cut-off value of 774 pg/ml, predictors of BAV were sRAGE>774 pg/ml (OR 7.7 95% CI 3.2-18.4) and smoking (OR 3.7 95% CI 1.4-9.7). The interaction between sRAGE and smoking was not significant (p=0.4). The model had a c-statistic of 0.83 (Table 7).

TABLE 7

Odds Ratio Estimates

| | Odds Ratio Estimates | |
| --- | --- | --- |
| | Point Estimate | 95% Wald Confidence Limits | |
| Age | 0.985 | 0.96 | 1.011 |
| Gender | 1.207 | 0.477 | 3.052 |
| sRAGE | 1.001 | 1.001 | 1.002 |
| Coronary Artery Disease | 0.291 | 0.072 | 1.173 |
| Smoking | 3.022 | 1.189 | 7.681 |
| Hypertension | 0.654 | 0.262 | 1.634 |
| Diabetes | 0.452 | 0.097 | 2.108 |
| Hyperhpidemia | 0.728 | 0.285 | 1.858 |

Figure 12:
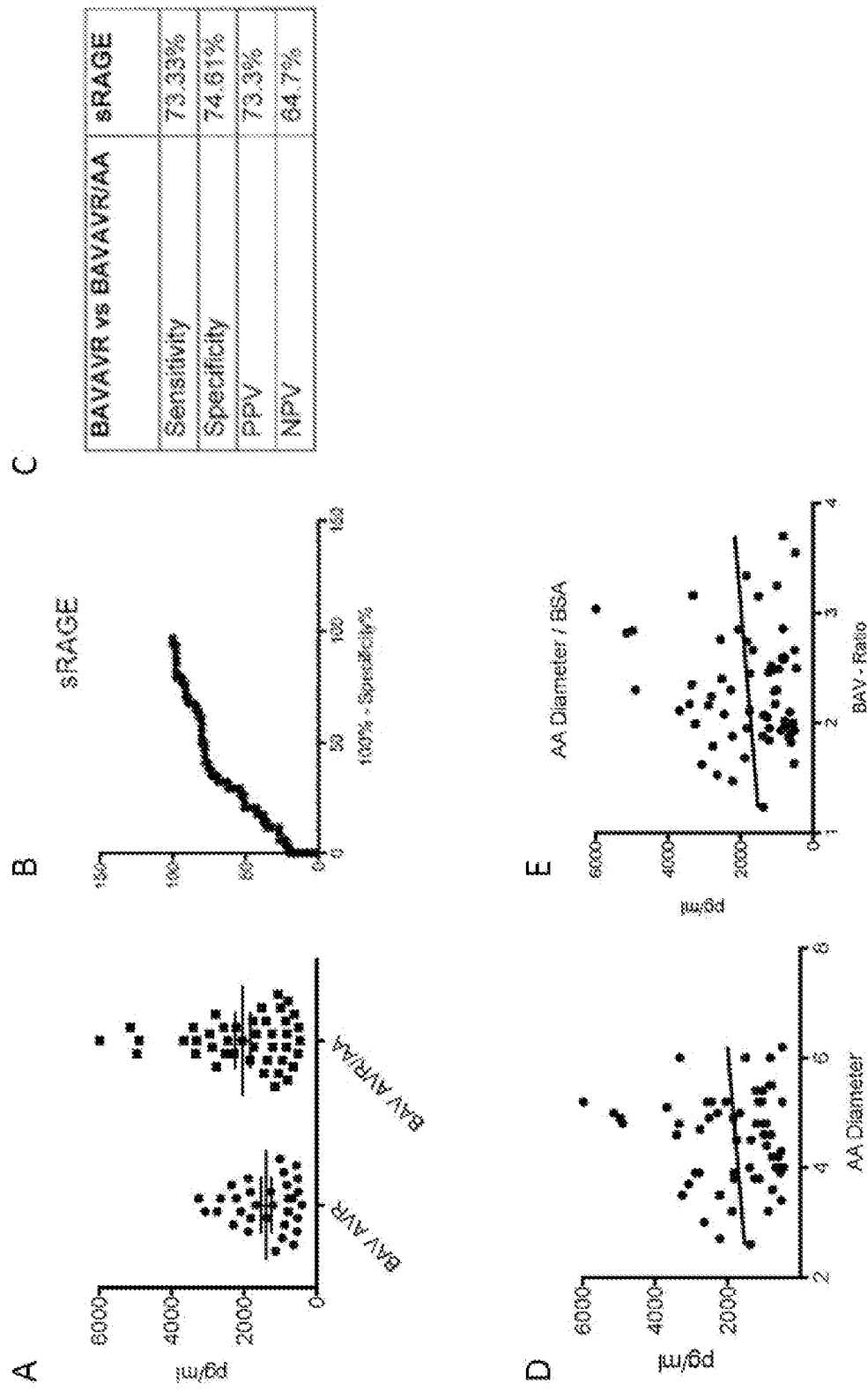
FIG. 12, comprising

Specific models for patients with or without severe aortic stenosis showed a similar predictive effect of sRAGE.

sRAGE Values Provide for the Identification of Patients Who Require Aggressive Surgical Intervention BAV patients were divided in two subgroups: those who underwent AVR due to AS or AI (n=32), and those who presented ascending aorta dilatation (ascending aneurysm>4.5 cm) concomitantly to AS or AI (n=42). As shown in FIG. 12A, BAV patients with only valvular pathology (mean ascending aorta diameter equal to 3.7 cm) presented sRAGE plasma values of 1288±142.3 pg/mL while patients who presented aortic valve pathology and associated aortopathy (mean ascending aorta diameter equal to 4.9 cm), show sRAGE levels equal to 2110±204.3 pg/mL (p=0.0027). Among the BAV group, sRAGE values higher than 1288 pg/mL allow for the identification of patients who require a more aggressive surgical intervention (AVR and ascending aorta/aortic arch repair or replacement) with 73.3% sensitivity and 74.61% specificity, and a PPV of 73.3% and a NPV of 64.7%. (FIGS. 12B and 12C)

Logistic regression was then performed to test whether sRAGE values may correlate with ascending aorta diameter or the ratio between ascending aorta diameter and body surface area (BSA). As shown in FIGS. 12D and 12E there is no correlation between sRAGE levels and ascending aorta diameter ($R^2$=0.007, p=0.51) or the ratio between ascending aorta diameter/BSA ($R^2$=0.011, p=0.42).

The results described above show that sRAGE levels are significantly higher in BAV patients compared to TAV. Accordingly, sRAGE levels greater than about, for example, 774 pg/ml is able to identify BAV patients with 82% sensitivity and 69% specificity.

According to the invention circulating levels of sRAGE can identify BAV patients with higher sensitivity and specificity than echocardiography and independently from the condition of the valve (insufficient, stenotic or heavily calcified). Furthermore higher levels of sRAGE were detected in BAV patients with aortic valve pathology and ascending aortopathies (aortic dilatation higher than 4.5 cm) when compared to BAV patients with only valvular pathologies. No linear correlation has been found between high levels of sRAGE and aortic diameter or aortic diameter/BSA in BAV patients with ascending aneurysm. sRAGE levels higher than 1288 pg/mL is a marker for the diagnosis of aortic complications in BAV patients with no linear correlation with aortic diameter.

The availability of a blood-based test to identify BAV disease opens the possibility to routinely screen BAV family members allowing an early identification and surveillance of this population. In addition, sRAGE ability to identify BAV patients and BAV-associated aortopathies is not affected by the presence of coronary artery disease and diabetes or by common risk factor for cardiovascular diseases such as hypertension, hyperlipidemia and smoking.

sRAGE Levels Provide for the Detection of Aortopathies in TAV and/or BAV Patients Statistical Analysis Statistical analysis was performed to evaluate differences in sRAGE values detected: 1) in TAV patients with ascending aorta diameter (AA) lower (n=47) or higher (n=14) than 5 cm; 2) in BAV patients with ascending aorta diameter lower (n=38) higher (n=34) than 4.5 cm; and 3) between BAV and TAV patients with ascending aorta dilatation. Comparison of means was carried by performing Student's t test using statistical software GraphPad Prism 5. Mean values are expressed in pg/ml±SEM.

Detection of Ascending Aorta Dilatation in TAV Patients

Figure 13:
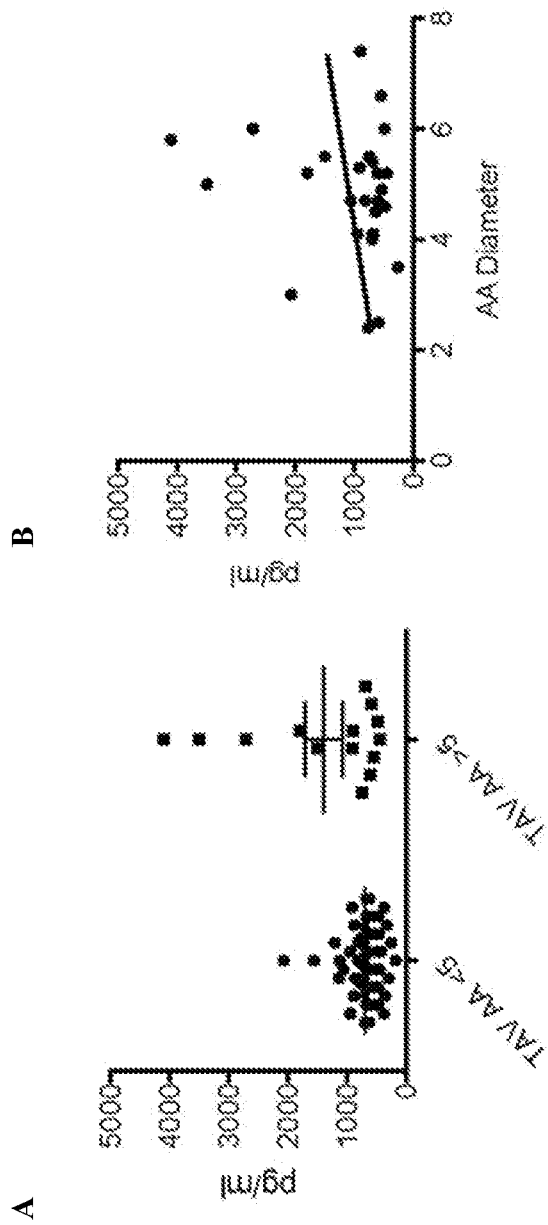
FIG. 13, comprising

Plasma level of sRAGE are significantly higher in TAV patients with ascending aorta diameter bigger than 5 cm (1398±321 pg/mL) when compared to TAV patients with an ascending aorta diameter smaller than 5 cm (703.4±49.5 pg/mL) (p=0.0496) (FIG. 13). There is no linear correlation between ascending aorta diameter and sRAGE values in TAV patients with and without dilatation (p=0.3628, $R^2$=0.03195). Thus, within the TAV population, high sRAGE values (1398±321 pg/mL) detect the presence of ascending aorta dilatation (>5 cm). This result shows that sRAGE values are higher in TAV patients with aneurysm when compared to those without aneurysm and confirm that sRAGE values do not linearly correlate with ascending aorta diameter.

Detection of Ascending Aorta Dilatation in BAV Patients

Figure 14:
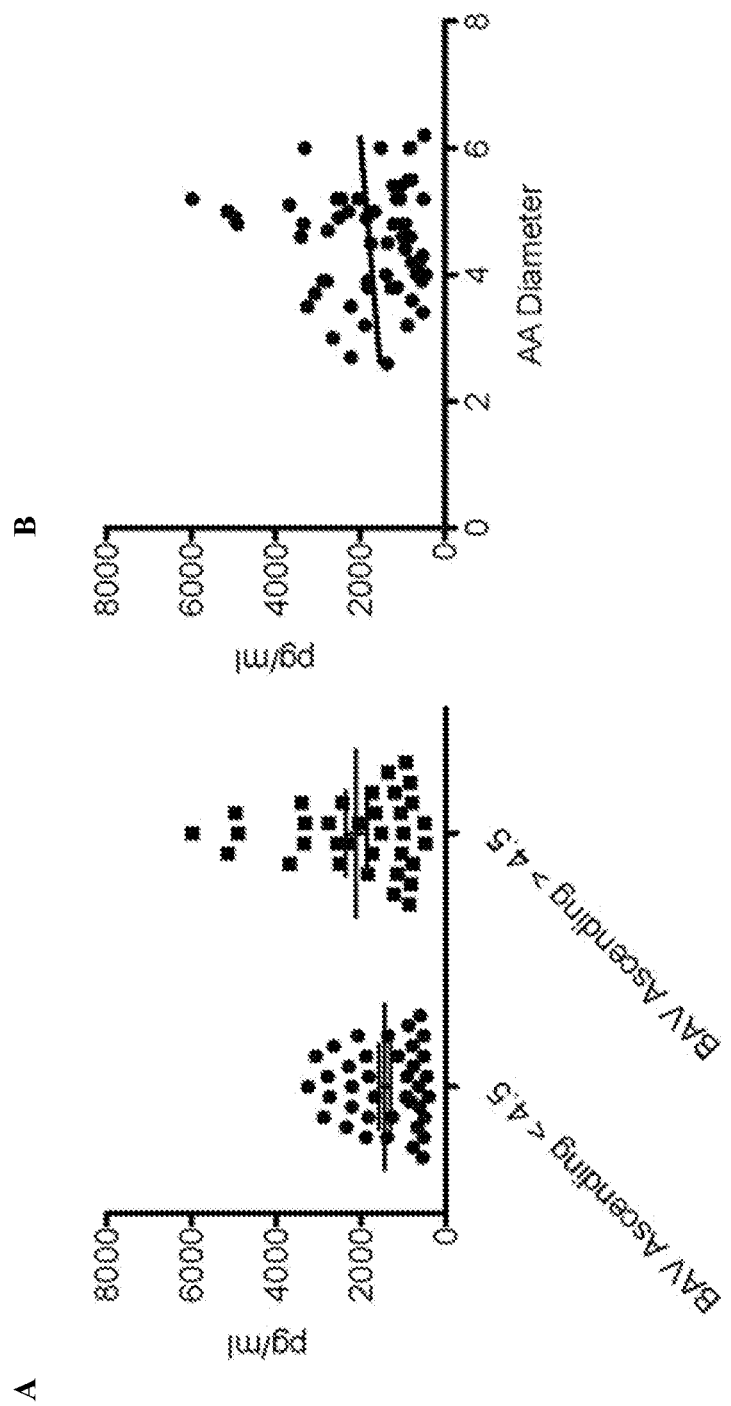
FIG. 14, comprising

Plasma level of sRAGE are significantly higher in BAV patients with ascending aorta diameter bigger than 4.5 cm (2116±250.4 pg/mL) when compared to BAV patients with an ascending aorta diameter smaller than 4.5 cm (1439±142 pg/mL) (p=0.0183) (FIG. 14). There is no linear correlation between ascending aorta diameter and sRAGE values in BAV patients with and without dilatation (p=0.5120, $R^2$=0.00071). Thus, sRAGE values are higher (2116±250.4 pg/mL) within the BAV population in patients with ascending aorta diameter greater than 4.5 cm. This result shows that BAV patients with a dilatation of the ascending aorta>4.5 cm have sRAGE values significantly elevated when compared to those with no dilatation. 4.5 cm is the current cut off for the decision to perform prophylactic surgery.

Figure 15:
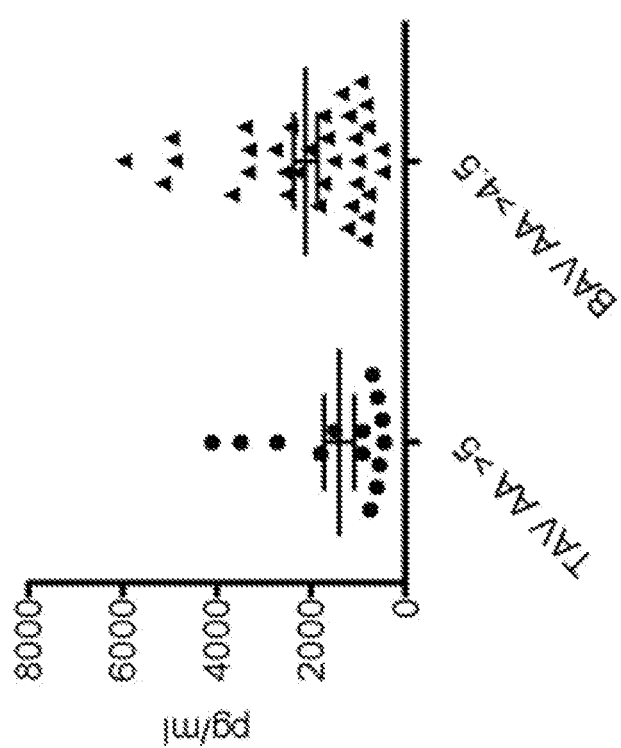
FIG. 15 depicts the sRAGE quantification in plasma samples of TAV and BAV patients with ascending aorta diameter (AA) higher than 5.5 and 4.5 cm, respectively. Dots represent values (pg/mL) for each patient±SEM. P=0.0303.

Discrimination Between BAV and TAV Patients that Meet the Criteria for Surgical Intervention of the Ascending Aorta Plasma level of sRAGE are significantly higher in BAV patients with ascending aorta diameter bigger than 4.5 cm (2116±250.4 pg/mL) when compared to TAV patients with an ascending aorta diameter bigger than 5 cm (1398±321 pg/mL) (p=0.0303) (FIG. 15). Thus, sRAGE values are higher in BAV patients with an ascending aorta diameter smaller than TAV patients, and discriminates between BAV and TAV patients that meet the criteria for surgical intervention of the ascending aorta. This result also shows that levels of sRAGE are already higher in BAV patients with ascending aorta dilatation lower than TAV patients.

Figure 16:
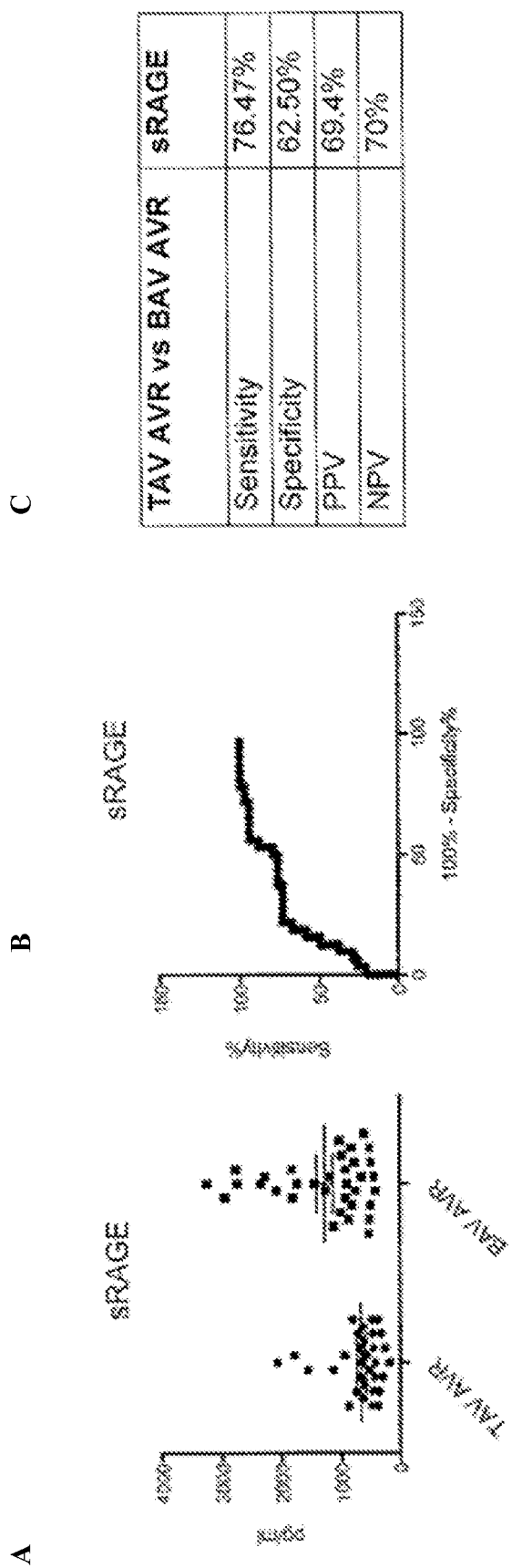
FIG. 16, comprising

Plasma Levels of sRAGE are Significantly Higher in BAV Patients Who Undergo Aortic Valve Replacement Compared to TAV Patients Who Undergo Aortic Valve Replacement Plasma level of sRAGE are significantly higher in BAV patients undergoing valvular replacement/repair (1280±138.3 pg/ml) when compared to TAV patients undergoing the same surgical intervention (685.4±75.61 pg/ml) (p=0.0004). (FIG. 16) Based on these data, a cutoff of 681.1 pg/ml allows for the successful discrimination between BAV and TAV patients with 76.47% sensitivity and 62.50% specificity, with a PPV of 69.4% and a NPV of 70%.

sRAGE Plasma Levels Identify BAV Patients with Higher Sensitivity and Specificity than Echocardiographic Analysis The sensitivity, specificity, Positive Predictive Value (PPV), and Negative Predictive Value (NPV) for echocardiography, sRAGE plasma quantification, and cardiac CT were compared. (See Table 8 below) Echocardiography has a 76.5% sensitivity and 60.6% specificity, with a PPV of 68.4% and a NPV of 95.2%. sRAGE quantification, on the other hand, has a 83.54% sensitivity and 67.44% specificity, with a PPV of 82.5% and a NPV of 69.05%.

TABLE 8

| | Echocardiography | sRAGE | Cardiac CT |
|---|---|---|---|
| Sensitivity | 76.5% | 83.54% | 94.1% |
| Specificity | 60.6% | 67.44% | 100% |
| PPV | 68.4% | 82.5% | 100% |
| NPV | 95.2% | 69.05% | 97.1% |

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of treating Bicuspid Aortic Valve (BAV) disease in a subject, the method comprising:
performing aortic valve replacement, performing ascending aorta surgery, administering a therapeutic compound, or a combination thereof to thereby treat the BAV disease in the subject,
wherein the subject has between about 600 pg/mL and about 1288 pg/ml of soluble Receptor for Advanced Glycation Endproducts (sRAGE) in a biological sample of the subject.

2. The method of claim 1, wherein the biological sample of the subject contains at least 681 pg/mL of sRAGE.

3. The method of claim 1, wherein the biological sample of the subject contains at least 15% greater sRAGE than a control biological sample.

4. The method of claim 3, wherein the control biological sample is from a subject with a tricuspid aortic valve (TAV).

5. The method of claim 1, further comprising imaging the aortic valve of the subject.

6. The method of claim 5, wherein the imaging is echocardiography, color Doppler transesophageal echocardiography, cardiac magnetic resonance imaging, computerized tomography, or a combination thereof.

7. The method of claim 1, wherein the administering a therapeutic compound reduces symptoms of the BAV disease.

8. The method of claim 1, wherein the biological sample is blood.

9. The method of claim 1, wherein between about 600 pg/mL and about 1288 pg/ml of sRAGE in the biological sample identifies the subject as having BAV with specificity of about 80% and sensitivity of about 70%.

10. A method for treating a subject with Bicuspid Aortic Valve (BAV) disease, the method comprising:
performing aortic valve replacement, performing ascending aorta surgery, administering a therapeutic compound, or a combination thereof to thereby treat the BAV disease in the subject,
wherein the BAV subject has at least 15% greater sRAGE than a control biological sample from a subject with a tricuspid aortic valve (TAV), and wherein the subject with BAV disease has between about 600 pg/mL and about 1288 pg/ml of soluble Receptor for Advanced Glycation Endproducts (sRAGE) in a biological sample of the BAV subject.

11. The method of claim 10, wherein the biological sample of the BAV subject contains at least 681 pg/mL of sRAGE.

12. The method of claim 10, further comprising imaging the aortic valve of the BAV subject.

13. The method of claim 12, wherein the imaging is echocardiography, color Doppler transesophageal echocardiography, cardiac magnetic resonance imaging, computerized tomography, or a combination thereof.

14. The method of claim 10, wherein the administering a therapeutic compound reduces symptoms of the BAV disease.

15. The method of claim 10, wherein between about 600 pg/mL and about 1288 pg/ml of sRAGE in the biological sample identifies the subject as having BAV with specificity of about 80% and sensitivity of about 70%.

16. A method of treating Bicuspid Aortic Valve (BAV) disease in a subject, the method comprising:
performing valve replacement and ascending aorta surgery to thereby treat the BAV disease in the subject,
wherein the subject has greater than about 1288 pg/ml of soluble Receptor for Advanced Glycation Endproducts (sRAGE) in a biological sample of the subject.

17. The method of claim 16, wherein the biological sample of the subject contains at least 1765 pg/mL of sRAGE.

18. The method of claim 16, wherein the biological sample of the subject contains at least 2209 pg/mL of sRAGE.

19. The method of claim 16, wherein the biological sample of the subject contains at least 15% greater sRAGE than a control biological sample.

20. The method of claim 19, wherein the control biological sample is from a subject with a tricuspid aortic valve (TAV).

21. The method of claim 16, further comprising imaging the aortic valve of the subject.

22. The method of claim 21, wherein the imaging is echocardiography, color Doppler transesophageal echocardiography, cardiac magnetic resonance imaging, computerized tomography, or a combination thereof.

23. The method of claim 16, wherein the biological sample is blood.

24. The method of claim 16, wherein greater than about 1288 pg/ml of sRAGE in the biological sample identifies the subject as needing aortic valve replacement and ascending aorta surgery with sensitivity of about 70% and specificity of about 75%.

* * * * *